United States Patent
Che et al.

(10) Patent No.: US 12,297,434 B1
(45) Date of Patent: May 13, 2025

(54) BIOMARKER FOR PREDICTING DRUG RESISTANCE OF BRUTON'S TYROSINE KINASE INHIBITORS AND APPLICATION THEREOF

(71) Applicant: Beijing Friendship Hospital, Capital Medical University, Beijing (CN)

(72) Inventors: Yiqun Che, Beijing (CN); Junhao Wei, Beijing (CN); Xinyu Han, Beijing (CN)

(73) Assignee: Beijing Friendship Hospital, Capital Medical University, Beijing (CN)

( * ) Notice: Subject to any disclaimer, the term of this patent is extended or adjusted under 35 U.S.C. 154(b) by 0 days.

(21) Appl. No.: 18/797,746

(22) Filed: Aug. 8, 2024

(51) Int. Cl.
| | |
|---|---|
| *C12N 15/113* | (2010.01) |
| *A61K 31/519* | (2006.01) |
| *A61K 31/7105* | (2006.01) |
| *A61K 31/713* | (2006.01) |

(52) U.S. Cl.
CPC ........ *C12N 15/1137* (2013.01); *A61K 31/519* (2013.01); *A61K 31/7105* (2013.01); *C12Y 207/01091* (2013.01); *C12Y 301/04012* (2013.01); *C12N 2310/531* (2013.01); *C12N 2320/31* (2013.01)

(58) Field of Classification Search
CPC .......... C12N 2310/531; C12N 2320/31; C12N 15/1137; C12Y 207/01091; C12Y 301/04012
See application file for complete search history.

(56) References Cited

FOREIGN PATENT DOCUMENTS

| | | |
|---|---|---|
| CN | 201912375 U | 8/2011 |
| CN | 102747156 A | 10/2012 |
| CN | 110426516 A | 11/2019 |
| CN | 115572768 A | 1/2023 |
| CN | 115976189 A | 4/2023 |
| KR | 20190048514 A | 5/2019 |
| KR | 20210066635 A | 6/2021 |

OTHER PUBLICATIONS

Rashid-Kolvear et al. (BMC Cancer. Jul. 22, 2010;10:390).*
Yu et al. (Int J Oncol. May 30, 2019;55(1):81-92).*
Zhao et al. (Gastroenterology, vol. 135, Issue 3, Sep. 2008, pp. 956-968).*
Yang Jing et al., "Application of Bcl-2 in molecular monitoring of B-cell lymphoma," Journal of Practical Medical Technology, Date of issue: Sep. 30, 2011, pp. 939-940, vol. 18, No. 9. Related claims: 1-10.

(Continued)

*Primary Examiner* — Terra C Gibbs
(74) *Attorney, Agent, or Firm* — Piloff Passino & Cosenza LLP; Rachel K. Piloff; Sean A. Passino

(57) ABSTRACT

A biomarker for predicting drug resistance of a BTK inhibitor and an application thereof are provided in the present disclosure, relating to the technical field of biomedicine. The biomarker is SMPD1 or SPHK1; the drug resistance of BTK inhibitor refers to the drug resistance of diffuse large B cell lymphom cells to the BTK inhibitor. This biomarker is used to predict sensitivity of diffuse large B cell lymphom cells to the BTK inhibitors.

1 Claim, 36 Drawing Sheets

Specification includes a Sequence Listing.

(56) References Cited

OTHER PUBLICATIONS

Yang Lan et al., "Role of SPHK1 Regulates Multi-drug Resistance of Small Cell Lung Cancer and Its Clinical Significance," China Journal of Lung Cancer, Date of issue: Nov. 30, 2014, pp. 769-777, vol. 17, No. 11. Related claims: 1-10.
Huajie Cai et al., "Sphingosine kinase 1: A novel independent prognosis biomarker in hepatocellular carcinoma," Oncology Letters, Date of issue: Dec. 31, 2017, pp. 2,316-2,322, vol. 13. Related claims: 1-10.
Office Action for China Patent Application No. 202410153890.3, mailed Mar. 18, 2024.
Notification to Grant Patent for China Patent Application No. 202410153890.3, mailed Apr. 1, 2024.
First Search Report for China Patent Application No. 202410153890.3, dated Mar. 13, 2024.
Supplementary Search Report for China Patent Application No. 202410153890.3, dated Mar. 22, 2024.

* cited by examiner

| Response | SMPD1 | | P |
| --- | --- | --- | --- |
| | + | − | |
| CR | 9 | 20 | 0.038 |
| Non-CR | 22 | 17 | |

FIG. 3B

| Response | SMPD1(mean±SD) (ng/mL) | P |
|---|---|---|
| CR | 313.9±36.6 | 0.008 |
| Non-CR | 338.1±36.0 | |

FIG. 3E

| Response | SPHK1 | | P |
| --- | --- | --- | --- |
| | + | − | |
| CR | 14 | 15 | 0.081 |
| Non-CR | 27 | 12 | |

FIG. 6D

| Response | SPHK1(mean±SD) (ng/mL) | P |
|---|---|---|
| CR | 38.0±5.8 | 0.006 |
| Non-CR | 41.9±5.5 | |

FIG. 6G

BIOMARKER FOR PREDICTING DRUG RESISTANCE OF BRUTON'S TYROSINE KINASE INHIBITORS AND APPLICATION THEREOF

CROSS-REFERENCE TO RELATED APPLICATIONS

This application claims priority to Chinese Patent Application No. 202410153890.3, filed on Feb. 4, 2024, the contents of which are hereby incorporated by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:
File name: 2024-4260 Sequence
Creation date: 1 Aug. 2024
Byte size: 20,299

TECHNICAL FIELD

The present disclosure relates to the technical field of biomedicine, and in particular to a biomarker for predicting drug resistance of Bruton's tyrosine kinase (BTK) inhibitors and an application thereof.

BACKGROUND

Non-Hodgkin lymphoma (NHL) is a malignant tumor originating from lymphohaematopoietic tissues. Recent years saw an increasing incidence of NHL, with diffuse large B cell lymphom (DLBCL) being one of the most common subtypes of NHL, accounting for 35% of NHL. Depending on the cellular origins and gene expression profiles, the DLBCL may be further classified into activated B-cell-like DLBCL (ABC-DLBCL), germinal center B-cell-like DLBCL (GCB-DLBCL), and the undifferentiated type.

There are great differences in the regulatory mechanism and carcinogenic pathway among the gene expression subgroups of DLBCL. The distinguishing feature of DLBCL is the aberrant activation of the B-cell receptor (BCR). In particular, the viability of ABC-DLBCL cells is strongly dependent on constitutive nuclear factor kappa-B (NF-kB) activation, which is a signature of ABC-DLBCL and may contribute to its resistance to immunochemotherapy. In various professional guidelines, the regime of rituximab in combination with chemotherapy (R-CHOP-like) is used as the standardized first-line treatment for DLBCL. The overall 5-year progression-free survival (PFS) rate of DLBCL is close to 60%, while the prognosis of patients with ABC-DLBCL is worse than that of patients with GCB-DLBCL, with a 5-year PFS % of less than 50%. In contrast to Europe and the United States, ABC-DLBCL accounts for about 70% of all DLBCL in East Asia, and it has been an urgent clinical challenge to study the resistance mechanism of ABC-DLBCL.

As a key kinase in the BCR pathway, Bruton's tyrosine kinase (BTK) drives the BCR signaling cascade and contributes to the activation of the downstream NF-κB and phosphatidylinositol-3-kinase (PI3K) pro-survival pathways in ABC-DLBCL. The BCR activity is connected to NF-kB by BTK, which is critical for the survival of ABC lines with chronic active BCR signaling. Ibrutinib is a selective covalent inhibitor of BTK that kills ABC-DLBCL cell lines by reducing NF-κB pathway activity. However, with the prolonged administration of R-CHOP in combination with BTK inhibitors, the problem of acquired drug-resistance is becoming increasingly apparent. The ibrutinib is a BTK inhibitor, which, in combination with R-CHOP, is effective in improving the prognosis of ABC-DLBCL patients aged less than 60 years, especially in patients with the MCD (based on the co-occurrence of MYD88L265P and CD79B mutations) and N1 (based on NOTCH1 mutations) gene subtypes. However, the mechanism of BTK inhibitor resistance is complex and has been reported to be associated with mutations in the BTK gene and alterations in molecular pathways within and outside the nucleus.

Sphingomyelin phosphodiesterase 1 (SMPD1) serves as a key enzyme in the sphingolipid metabolic cycle, and SMPD1 converts sphingomyelin, a lipid cell membrane component, to ceramide. In cancer cells, SMPD1-mediated ceramide production is important for apoptosis, proliferation, and immune regulation and tumor metastasis, and SMPD1 shows potential as a therapeutic target in glioblastoma, non-small-cell lung cancer, and colorectal cancer, and so on. SMPD1 and ceramides perform critical functions in signal transduction in response to many stress and apoptotic stimuli. The ceramide produced catalytically by SMPD1 induces membrane reorganization and the formation of ceramide-rich lipid rafts, and these membrane domains will aggregate activated receptors and capture and enrich intracellular signaling molecules at the sites of receptors and associated signaling molecules to amplify cellular signaling. As a precursor of other biologically active sphingolipids, ceramide may be converted to sphingosine-1-phosphate (SIP), whereas sphingosine kinase 1 (SPHK1), as the main SIP-producing enzyme, promotes cancer development and progression.

SMPD1 deficiency usually leads to type A and type B Niemann-Pick diseases, but little is known about the role in anti-tumor immune responses, and the correlation between SMPD1 and ABC-DLBCL BTK inhibitor resistance has not been reported in the literature, the expression and function of the SMPD1/NF-κB pathway and the intermediate molecule SPHK1 in ABC-DLBCL are unclear, and whether there is a correlation with ABC-DLBCL BTK inhibitor resistance is unknown.

SUMMARY

The objective of the present disclosure is to provide a biomarker for predicting drug resistance of BTK inhibitors and an application thereof, so as to solve the problems existing in the prior art, and the biomarker may be used for predicting the sensitivity of diffuse large B cell lymphom cells to BTK inhibitors, thus being beneficial to the reasonable selection of treatment schemes for diffuse large B cell lymphom.

In order to achieve the above objectives, the present disclosure provides the following technical schemes.

The present disclosure provides a biomarker for predicting drug resistance of a BTK inhibitor, where the biomarker is SMPD1 or SPHK1; and the drug resistance of the BTK inhibitor refers to the drug resistance of diffuse large B cell lymphom cells to the BTK inhibitor.

Optionally, an elevated expression of the SMPD1 or the SPHK1 suggests increased resistance of the diffuse large B cell lymphom cells to the BTK inhibitor.

Optionally, the BTK inhibitor is zebutinib.

The present disclosure also provides an application of a reagent for detecting a content of the biomarker in diffuse large B cell lymphom tissues or serum in preparing a product for predicting resistance of diffuse large B cell lymphom cells to the BTK inhibitor.

Optionally, the product is a reagent or a kit.

The present disclosure also provides a product for predicting the drug resistance of diffuse large B cell lymphom cells to the BTK inhibitor, including a reagent for detecting a content of the biomarker in diffuse large B cell lymphom tissues or serum.

Optionally, the product is a reagent or a kit.

The present disclosure also provides an application of a reagent for reducing an expression amount of the SMPD1 and/or SPHK1 in preparing a medicine for improving a sensitivity of diffuse large B cell lymphom cells to the BTK inhibitor.

Optionally, the reagent is a short hairpin ribonucleic acid (shRNA) with a nucleotide sequence as shown in SEQ ID NO.6 or SEQ ID NO.7.

The present disclosure also provides a composition for treating diffuse large B cell lymphom, which includes a reagent for reducing an expression amount of SMPD1 and/or SPHK1 and a BTK inhibitor.

The present disclosure achieves the following technical effects.

According to the present disclosure, the expression and function of SMPD1 in ABC-DLBCL is investigated, and it is found that SMPD1 is highly expressed in ABC-DLBCL tissues and patients' sera, and the mRNA and protein expression of SMPD1 is detected in ABC-DLBCL cell lines in vitro, and it is also found that SMPD1 is highly expressed and promotes the proliferation of tumor cells and drug resistance in ABC-DLBCL; by further knocking down/overexpressing SMPD1, it is revealed that SMPD1 mediates zebutinib resistance through the activation of NF-κB via the intermediate molecule SPHK1. The above results suggest that SMPD1 or SPHK1 may serve as biomarkers for predicting the sensitivity of diffuse large B cell lymphom cells to BTK inhibitors, thus facilitating the rational selection of treatment regimens for diffuse large B cell lymphom.

The present disclosure also identifies the pathway by which the new SMPD1/NF-κB pathway mediates ABC-DLBCL resistance to BTK inhibitors, which provides new ideas for the development of new targeted drugs and is expected to improve the status quo of BTK inhibitor resistance. Key molecules of the SMPD1/NF-κB signaling pathway have the potential to become markers for dynamic monitoring of resistance to BTK inhibitors and are expected to serve as factors in the mid-term evaluation of therapeutic regimens and provide prognostications of the final outcome of treatment.

BRIEF DESCRIPTION OF THE DRAWINGS

In order to explain the embodiments of the present disclosure or the technical scheme in the prior art more clearly, the drawings needed in the embodiments will be briefly introduced below. Obviously, the drawings described below are only some embodiments of the present disclosure, and other drawings may be obtained according to these drawings without creative work for ordinary people in the field.

Figure 3B:
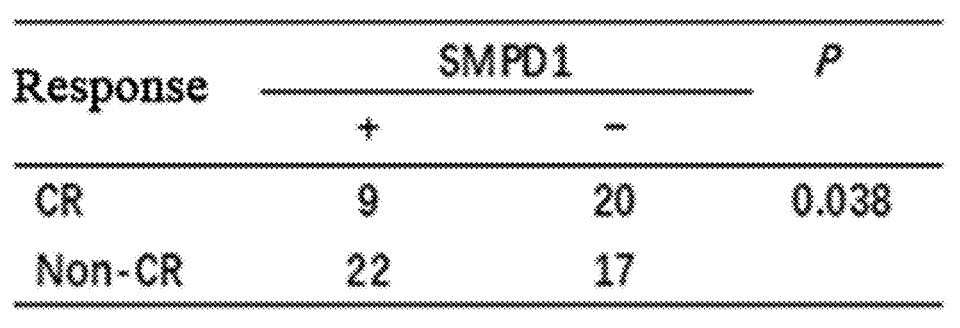

FIG. 3B shows the significant negative correlation between high SMPD1 protein expression (IHC) and clinical complete remission (CR).

FIG. 3E illustrates a significant negative correlation between high serum concentrations of SMPD1 and CR.

FIG. 6D shows a trend of negative correlation between high SPHK1 protein expression (IHC) and clinical complete remission (CR).

FIG. 6G illustrates the significant negative correlation between serum SPHK1 concentration and CR.

DETAILED DESCRIPTION OF THE EMBODIMENTS

Figure 1A:
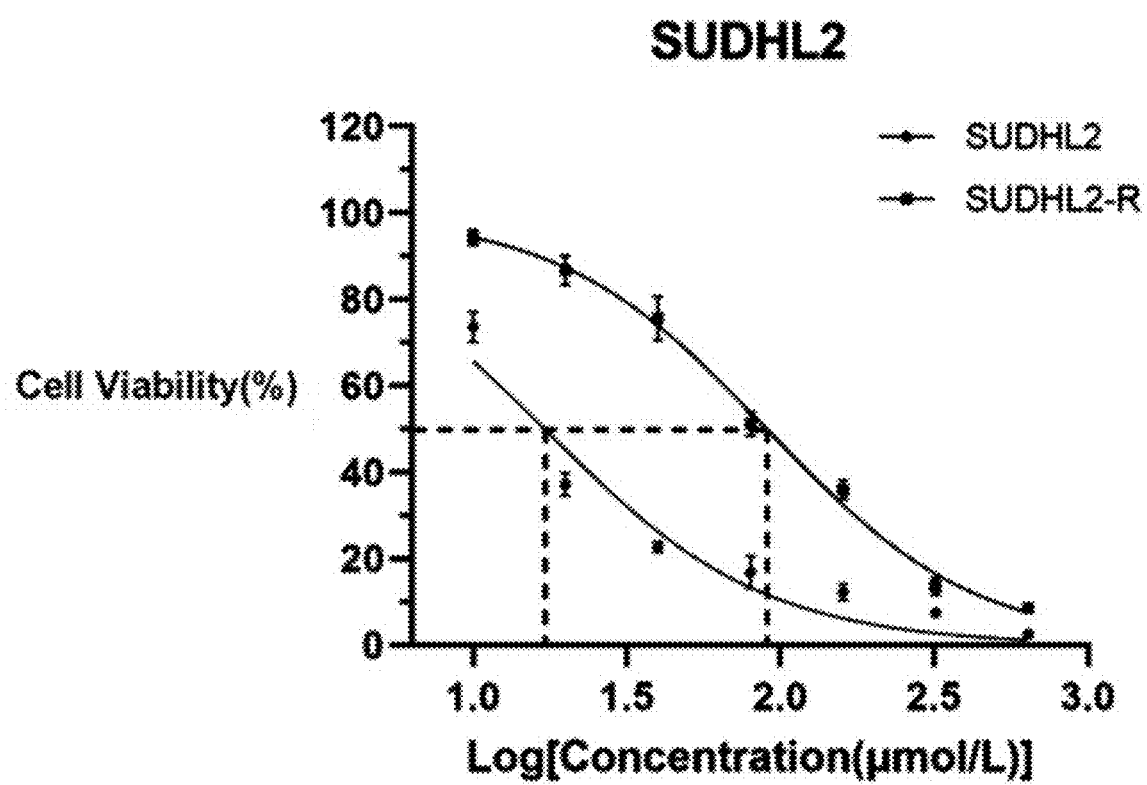
FIG. 1A shows the $IC_{50}$ curve of zebutinib in the BTK inhibitor-resistant ABC-DLBCL cell line SUDHL2-R.

A number of exemplary embodiments of the present disclosure will now be described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which this disclosure relates. Although the present disclosure only describes the preferred methods and materials, any methods and materials similar or equivalent to those described herein may also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the disclosure. The description and embodiments of the present disclosure are exemplary only.

The terms "including", "comprising", "having" and "containing" used in this specification are all open terms, which means including but not limited to.

Embodiment 1

1. Materials and Methods 1.1 Cell Lines and Patient Specimens

Human ABC-DLBCL cell lines (SUDHL2, U2932 and OCI-LY10) are purchased from American Type Culture Collection (ATCC) cell bank. The BTK inhibitor-resistant ABC-DLBCL-R cell line is constructed according to the drug concentration gradient increment method, and the BTK inhibitor used in the present disclosure is zebutinib. From January 2021 to June 2023, 68 patients with relapsed/refractory (R/R) DLBCL who failed to receive standardized R-CHOP regimen and received second-line chemotherapy combined with BTK inhibitors were selected from Beijing Friendship Hospital affiliated to Capital Medical University and Cancer Hospital of China Academy of Medical Sciences. All the patients were diagnosed according to the 2016 revision of the WHO classification of lymphoid neoplasms. Before the study, written informed consent was obtained from each patient and healthy volunteer.

1.2 Case Inclusion and Exclusion Criteria 1.2.1 Case Inclusion Criteria:
  (1) confirmed by biopsy as DLBCL;
  (2) patients with R/R DLBCL who failed to receive standardized R-CHOP-like chemotherapy and received second-line chemotherapy combined with BTK inhibitors;
  (3) no serious diseases of the heart, liver or kidney system; and
  (4) with evaluable lesions and expected survival>3 months.

Definition of relapse: relapse refers to lymphoma that recurs after complete remission (CR) after initial chemotherapy. There is no recognized and clear definition of relapsed/refractory DLBCL, and according to the references of the present disclosure, the diagnosis is made when any one of the following is met:
  (1) after 4 courses of chemotherapy according to the standard scheme, the tumor shrinks by less than 50% or the disease progresses;
  (2) CR is reached by standard regimen of chemotherapy, but relapse occurs within six months;
  (3) two or more relapses after CR; and
  (4) relapse after hematopoietic stem cell transplantation.

1.2.2 Exclusion Criteria:
  (1) other types of NHL;
  (2) contraindications to chemotherapy;

(3) mental illness;
(4) HIV history, active or chronic hepatitis C or B, pregnancy or lactation; and
(5) cases with incomplete case data and follow-up information.

1.2 Methods

1.2.1 Establishment of Drug-Resistant Cell Lines

The drug concentration gradient is used to induce zebutinib resistance to BTK inhibitor in ABC-DLBCL cell lines (SUDHL2, U2932 and OCI-LY10). Tumor cells in the logarithmic growth phase are taken, and zebutinib at a starting concentration of 2 micromoles per liter (μmol/L) (about 1/10 of the $IC_{50}$ of the parental cell line) is added to act for 24 hours (h). The culture medium is discarded, washed twice with PBS, and replaced with a drug-free medium, and after the growth of the cells is restored, the cells are passaged and again subjected to the action of the drug at a low concentration for 24 h, and the above drug shocks are repeated until the cells are capable of growing stably at this concentration. After that, the drug concentration is increased manifold to continue the culture, and each concentration has 6 times of shock. The drug induction is lasted for 8 months until the $IC_{50}$ of drug-resistant cells reaches more than 5-fold of the parental cells, and the construction of zebutinib-resistant cell line ABC-DLBCL-R (SUDHL2-R, U2932-R and OCI-LY10-R) is completed.

1.2.2 Cell Culture

ABC-DLBCL and ABC-DLBCL-R cell lines are cultured in an incubator at 37 degrees Celsius (° C.) and 5% CO2. The medium is RPMI-1640 medium containing 10% fetal bovine serum (Invitrogen, San Diego, California, USA), 100 U/mL penicillin (thermo) and 50 μg/mL streptomycin (thermo). Experiments are conducted when the cells reach the logarithmic growth phase.

1.2.3 Screening of Differential Metabolites

Targeted metabonomics detection is carried out on parental cells and drug-resistant cells to screen differential metabolites. Firstly, a disease molecular database of more than 1,000 substances in metabolomics is established, which contains sixteen categories of metabolites such as fatty acids, amino acids, polypeptides and analogs, nucleosides, nucleotides and analogs, and phospholipids, etc., comprehensively covering polar and nonpolar, hydrophilic and hydrophobic metabolites, and broadly including important pathways related to disease, such as energy metabolism, lipid metabolism, amino acid metabolic pathways, etc. The detection is performed by Liquid chromatography-tandem mass spectrometry (LC-MS), and the LC-MS section is based on a Shimadzu NexeraX2 LC-30AD system, applying selective reaction/multi-reaction monitoring (SRM/MRM) technology to detect and analyze a specific group of metabolites in a targeted and specific manner using a standard as a reference to obtain the absolute quantitative results of the target metabolites. The metabolites of parental and drug-resistant cell lines are then compared for differences and analyzed by bioinformatics, and the metabolites and metabolizing enzymes with the most significant and clinically meaningful differences are screened.

1.2.4 Immunohistochemical Staining and Enzyme-Linked Immuno Sorbent Assay (ELISA)

The antibodies used in immunohistochemistry and immunohistochemical staining are as follows: anti-SMPD1 antibody (1:100, ab272729, Abcam) and anti-SPHK1 antibody (1:100, 12071S, CST). The PV-9000 polymer detection system (PV9000, ZSGB-BIO) is used for immunostaining visualization. At the same time, the results of histological experiments are verified at the serum level by using SMPD1 kit (ELH-SMPD1) and SPHK1 kit (ELH-SPHK1), and the serum concentrations of SMPD1 and SPHK1 of the above patients and corresponding matched healthy subjects are detected by ELISA.

1.2.5 Synthesis and Plasmid Construction of Small Interfering RNA (siRNA)

The siRNA used for SMPD1 and SPHK1 genes and the non-silencing siRNA of the control are provided by GenePharma (Shanghai, China), and the lentiviral vector expressing SMPD1 and SPHK1 or the shRNA of the control is constructed by GenePharma. The sequences of siRNA used are as follows:

SMPD1-Homo-9015-F: 5'-GCCACACUCAUGUG-GAUGAAUTT-3' (SEQ ID NO.1);
SMPD1-Homo-9015-R: 5'-AUUCAUCCACAUGAGU-GUGGCTT-3' (SEQ ID NO.2).
SMPD1-Homo-1740-F: 5'-CAGGGCUCGAGAAACC-UAUTT-3' (SEQ ID NO.3);
SMPD1-Homo-1740-R: 5'-AUAGGUUUCUCGAGCC-CUGTT-3' (SEQ ID NO.4).
SPHK1-homo-3675-F: 5'-GCAGCUUCCUUGAAC-CAUUAUTT-3' (SEQ ID NO.5);
SPHK1-homo-3675-R: 5'-AUAAUGGUU-CAAGGAAGCUGCTT-3' (SEQ ID NO.6).

The non-silencing siRNA sequence used as control is: 5'-TTCTCCGAACGTGTCACGT-3' (SEQ ID NO.7). The shRNA sequences used are as follows:
shRNA-SMPD1-1: 5'-CAGGGCTCGAGAAACCT-ATTT-3' (SEQ ID NO.8);
shRNA-SMPD1-2: 5'-GCCACACTCATGTGGAT-GAATTT-3' (SEQ ID NO.9).
shRNA-SPHK1-1: 5'-GCAGGCAUAUGGAGUAU-GATT-3' (SEQ ID NO.10).
shRNA-SPHK1-2: 5'-UCAUACUCCAUAUGC-CUGCTT-3' (SEQ ID NO.11).
Scramble sequence is: 5'-GGATCATCATGC-TATGCAGTT-3' (SEQ ID NO.12).

1.2.6 Transfection and Lentivirus Transduction

The siRNA is introduced into the target cells using lipofectamine 2000 (Life Technologies, Carlsbad, California, USA). The final concentration of siRNA for SMPD1 and SPHK1 gene knockout is 100 nano-meters (nM). After 48 h, the cells are collected for subsequent analysis. ABC-DLBCL cells are transduced with lentivirus, and cell lines stably expressing SMPD1-shRNA and SPHK1-shRNA sequence are screened with 1 μg/mL puromycin (Sigma-Aldrich), and the control scramble-shRNA (sh-scramble), followed by culture for one week.

1.2.7 Cell Survival Rate and Colony Formation Test

Cell activity is measured using a cell counting kit-8 (CCK-8, Dojindo, Japan). Cells are inoculated into 96-well plates, and the cell density of each well is 2000 cells in triplicate. The absorbance at 450 nm is measured by ELX808 microplate spectrophotometer (BioTekInstruments, Winooski, VT, USA). Colony formation experiment: cells are inoculated into a 6-well plate with 500 cells per well, three copies in one group, and cultured for 10-14 days to form colonies, followed by freeze-storage in formaldehyde and staining with crystal violet, and the visible colonies are counted.

1.2.8 Protein Western Blot

Total protein is separated from protease inhibitor (Bimake, B14001) and phosphatase inhibitor (Bimake, B15001) by RIPA buffer (Applygen, Beijing, China). Protein western blot is carried out according to the standard procedure, and the primary antibodies used are as follows: anti-SMPD1 (1:1000, ab272729, Abcam), anti-SPHK1 (1:1000, 12071S, CST) and anti-p-NF-κB p65 (Ser536) (1:1000, 3033S CST), anti-NF-κB p65 (1:1000, 8242S, CST), anti-IκBα (1:1000, 4812S, CST). β-actin (1:1000, 4970S, CST) is used as a loading control. Secondary antibody: Horseradish enzyme labeled goat antibody IgG (H+L) (1:5000, Zb-2301, ZSGB-Bio). Super chemiluminescence (ECL) detection reagent (Thermo Fisher) is used to display the signal, and AMERSHAM ImageQuant 800 is used for western blot quantitative analysis.

1.2.9 RNA Extract and Real-Time PCR

After zebutinib treatment, total RNA is extracted by RNApure tissue cell kit (Cwbiotech, Beijing, China). Using the extracted RNA as a template, the reverse transcription reaction is carried out by using HiFiScript cDNA synthesis kit (Cwbiotech). SYBR®Fast qPCR Mix (TaKaRa, Shiga, Japan) and CFX96 real-time system (Bio-Rad) are used for real-time quantitative RT-PCR analysis. The relative mRNA expression of target gene is normalized to endogenous reference (β-actin), and the primer sequences used in the present disclosure are as follows:

SPHK1-F-1: 5'-AACTACTTCTGGATGGTCAG-3' (SEQ ID NO.13);
SPHK1-R-1: 5'-TCCTGCAAGTAGACACTAAG-3' (SEQ ID NO.14);
SPHK1-F-2: 5'-GCTGCGAAGTTGAGCGAAAA-3' (SEQ ID NO.15);
SPHK1-R-2: 5'-GGCTGGACCCAGTCGG-3' (SEQ ID NO.16);
SMPD1-F-1: 5'-AAAGCCCAAATGCTGCTGTG-3' (SEQ ID NO.17);
SMPD1-R-1: 5'-ACAGCTCCTGTCTTGTCTGC-3' (SEQ ID NO.18);
SMPD1-F-2: 5'-CTGCGCACCCTCAGAATTGG-3' (SEQ ID NO.19);
SMPD1-R-2: 5'-TGTCTCCTCGATCCTCAGCA-3' (SEQ ID NO.20);
β-actin-F: 5'-GAGCACAGAGCCTCGCCTTT-3' (SEQ ID NO.21);
β-actin-R: 5'-TCATCATCCATGGTGAGCTGG-3' (SEQ ID NO.22).

1.2.10 Sedimentation and Mass Spectrometry Analysis of GST Fusion Protein

Construction of pGEX-KG-SMPD1: firstly, the double restriction sites of SMPD1 gene are analyzed and determined, then the upstream and downstream primers of PCR are designed, the SMPD1 gene is amplified by PCR, and the SMPD1 gene is introduced into a pGEX-KG vector (purchased from Genomeditech (Shanghai) Co., LTD.) through the steps of restriction, recovery, ligation and transformation identification, so as to realize the construction of pGEX-KG-SMPD1.

pGEX-KG vector and pGEX-KG-SMPD1 plasmid are transformed into competent cell BL21 (DE3) respectively, and the expression and purification of GST fusion target protein are induced to obtain pGEX-KG no-load-GST and pGEX-KG-SMPD1-GST respectively.

Equal amounts of pGEX-KG no-load-GST and pGEX-KG-SMPD1-GST fusion protein solutions are taken and added to 40 μL of GST agarose beads, respectively, and incubated for 6 h at 4° C. with flip-flop incubation, followed by washing with an appropriate amount of 1×PBS, and respectively incubating with cell lysate at 4° C. overnight with flip-flop incubation, then the GST agarose beads are washed once with nondenaturing lysate, and the GST agarose beads are then washed five times with an appropriate amount of 1×PBS. Then, 2×protein loading buffer is added, heated at 100° C. for 5 min, and the protein set interacting with SMPD1 is obtained by instantaneous centrifugation, and then separated by SDS-PAGE electrophoresis. After being dyed and decolorized by Coomassie brilliant blue dye, the difference bands of the two groups are cut separately with the no-load group as the control, and the high-abundance protein and the low-abundance protein are stored separately for subsequent mass spectrometry identification.

1.2.11 Immunoprecipitation Method

Total proteins are separated by using an undenatured lysis buffer (Applygene) containing protease inhibitors. Protein G agarose beads are incubated with anti-SMPD1 (Abcam), anti-SPHK1 (CST) and mouse or rabbit IgG (Applygen) at room temperature for 1 h, and then protein lysate is added and incubated at 4° C. overnight. After that, the immune precipitate is collected by centrifugation and washed with PBST. Protein blot analysis is then performed on the mixture.

1.2.12 Statistical Analysis

Statistical analysis is performed using SPSS 23.0 and graphs are plotted using GraphPad Prism version 8.0 and R software. Each experiment is repeated three times and experimental data are expressed as mean±standard deviation (SD). The SMPD1 and SPHK1 expression levels before and after treatment are compared using the paired t-test (normal distribution) or the Wilcoxon paired signed rank test (non-normal distribution), and the SMPD1 and SPHK1 expression levels of drug-resistant/sensitive cell lines are compared using the Mann-Whitney U test. Correlation analysis between SMPD1, SPHK1 expression levels and clinical prognosis is conducted by Pearson correlation test. Metabolites with both multidimensional statistical analysis VIP>1 and univariate statistical analysis P<0.05 are selected according to the orthogonal principal component analysis-discriminant analysis (OPLS-DA) model.

Figure 1B:
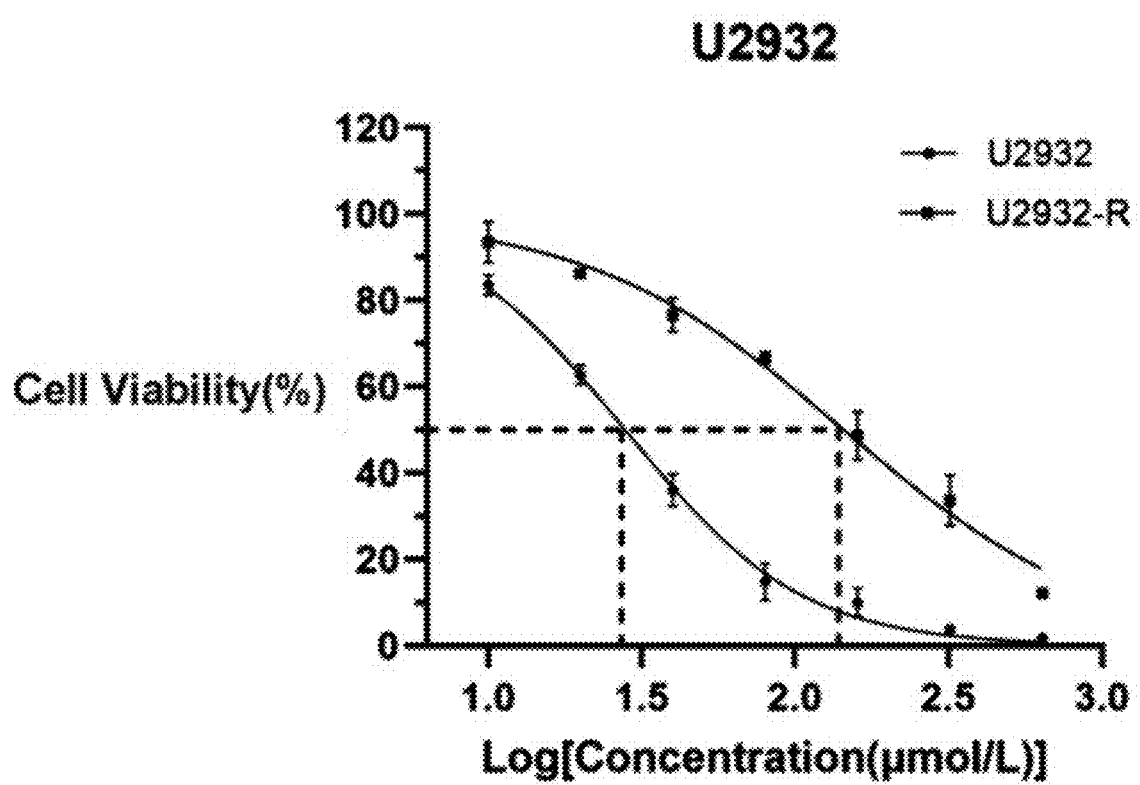
FIG. 1B shows the $IC_{50}$ curve of zebutinib in the BTK inhibitor-resistant ABC-DLBCL cell line U2932-R.
Figure 1C:
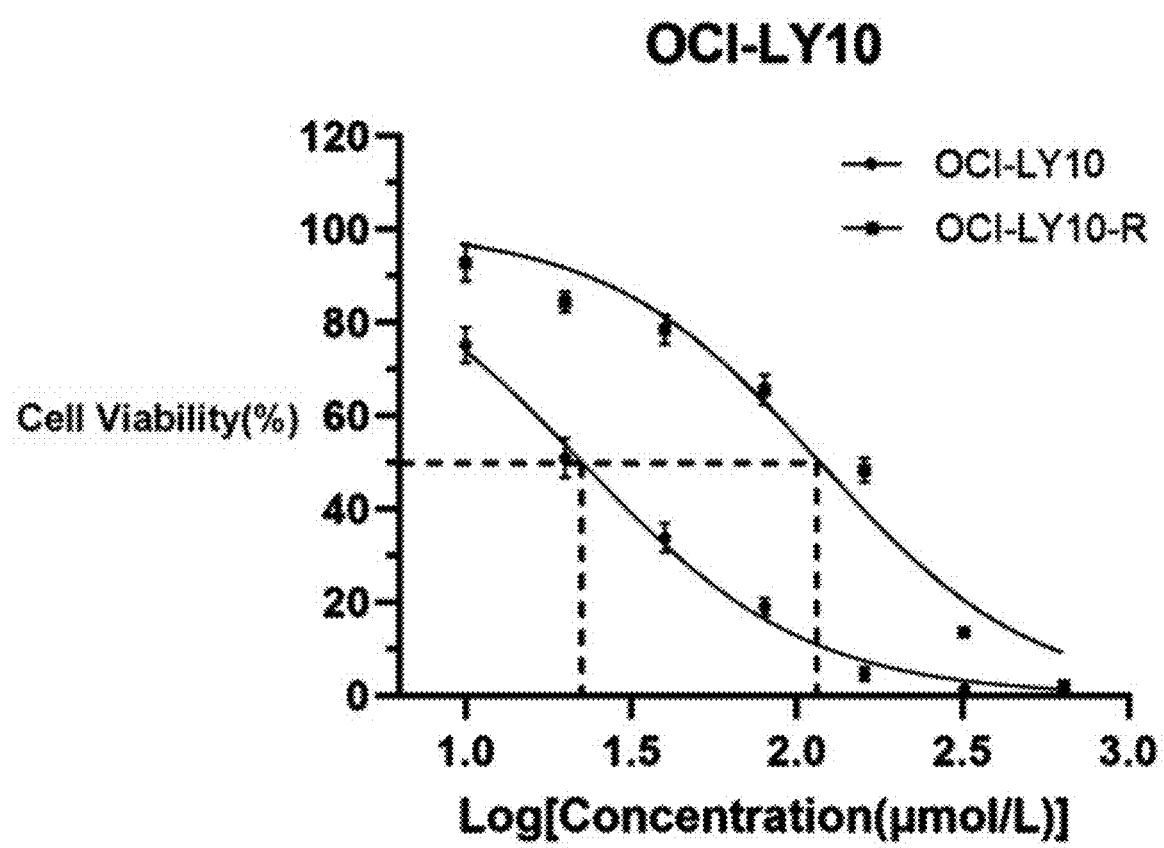
FIG. 1C shows the $IC_{50}$ curve of zebutinib in the BTK inhibitor-resistant ABC-DLBCL cell line OCI-LY10-R.
Figure 1D:
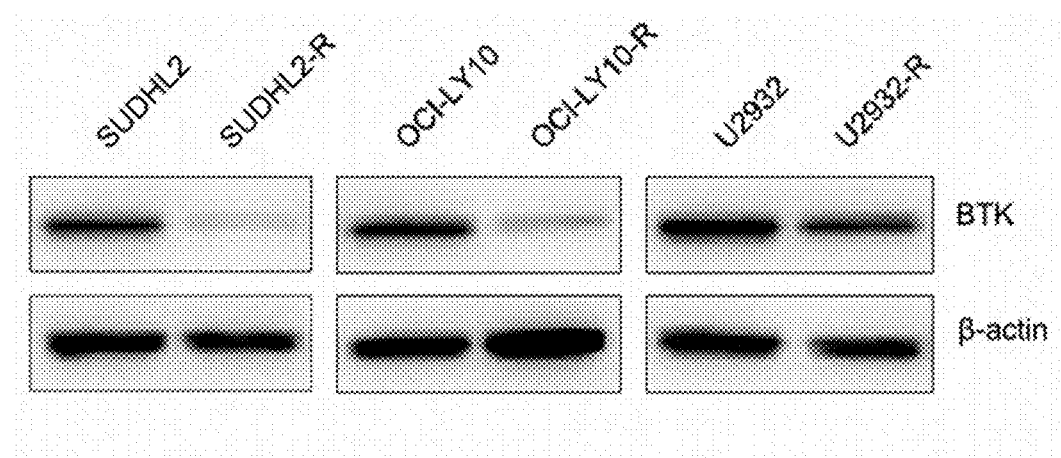
FIG. 1D shows the expression levels of BTK protein in BTK inhibitor sensitive and resistant ABC-DLBCL cell lines.

2. Results 2.1 Obvious Abnormal Sphingomyelin Metabolism of ABC-DLBCL Cell Line with BTK Inhibitor Resistance In the present disclosure, the drug resistance of ABC-DLBCL cell lines (SUDHL2, U2932 and OCI-LY10) is induced by using BTK inhibitor zebutinib, and three zebutinib-resistant cell lines (SUDHL2-R, U2932-R and OCI-LY10-R) are established (see FIG. A and FIG. 1B). The half maximal inhibitory concentration ($IC_{50}$) of zebutinib on cells is detected by CCK8 method, and the resistance index (RI) of drug-resistant cells is calculated, where RI=$IC_{50}$ of drug-resistant cell line/$IC_{50}$ of parental cell line. The $IC_{50}$ of SUDHL2 is 17.09 μmol/L, the $IC_{50}$ of SUDHL2-R is 90.29 μmol/L, and RI is 5.28. The $IC_{50}$ of U2932 is 27.98 μmol/L, the $IC_{50}$ of U2932-R is 144.0 μmol/L and the RI is 5.14. The $IC_{50}$ of OCI-LY10 is 22.48 μmol/L, the $IC_{50}$ of OCI-LY10-R is 117.5 μmol/L, and RI is 5.23. RI>5 suggests that the drug resistance of drug-resistant cell lines meets the requirements of drug-resistant strains, and the results show that all three cell lines meet the requirements of drug-resistant cell lines (RI>5). In addition, after zebutinib is applied to ABC-DLBCL cell line to construct drug-resistant cell lines, the BTK levels of drug-resistant cell lines SUDHL2-R, U2932-R and OCI-LY10-R are significantly decreased with significant inhibition, suggesting that BTK inhibitors are no longer effective in targeting the BTK targets of drug-resistant cells (see FIG. 1B).

Figure 2A:
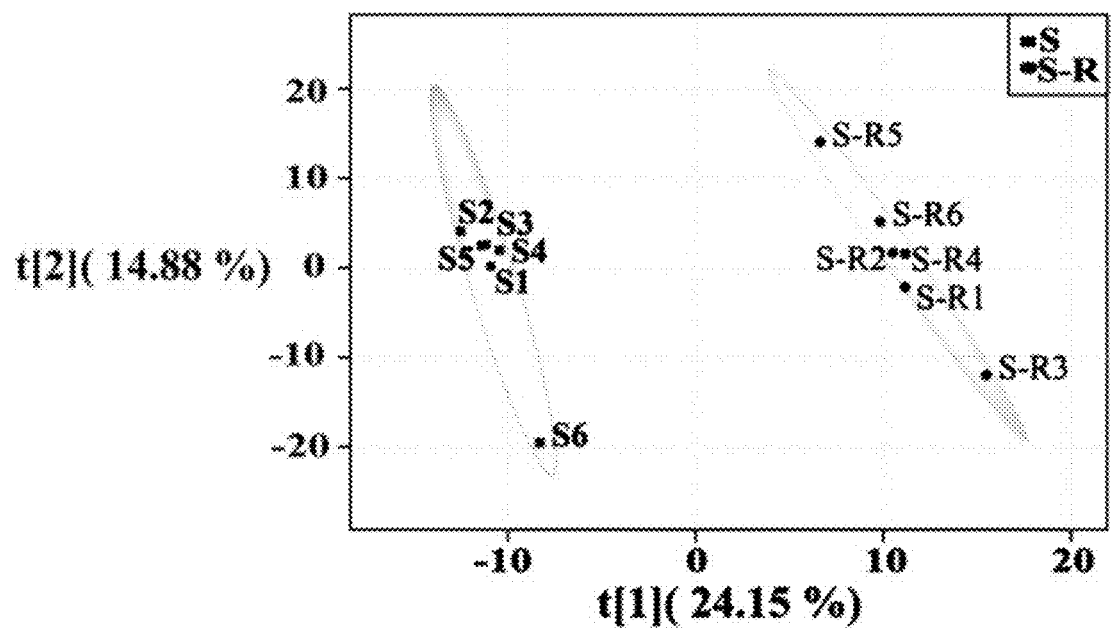
FIG. 2A is the partial least squares discriminant analysis (PLS-DA) diagram of SUDHL2-S and SUDHL2-R.
Figure 2B:
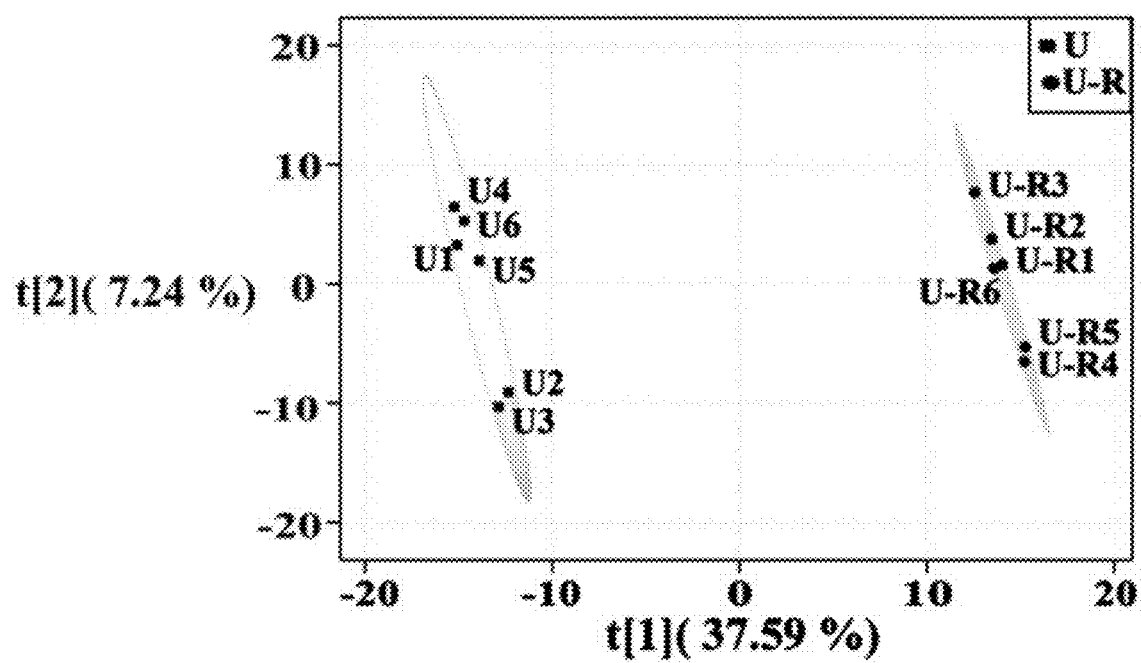
FIG. 2B is the PLS-DA diagram of U2932-S and U2932-R.
Figure 2C:
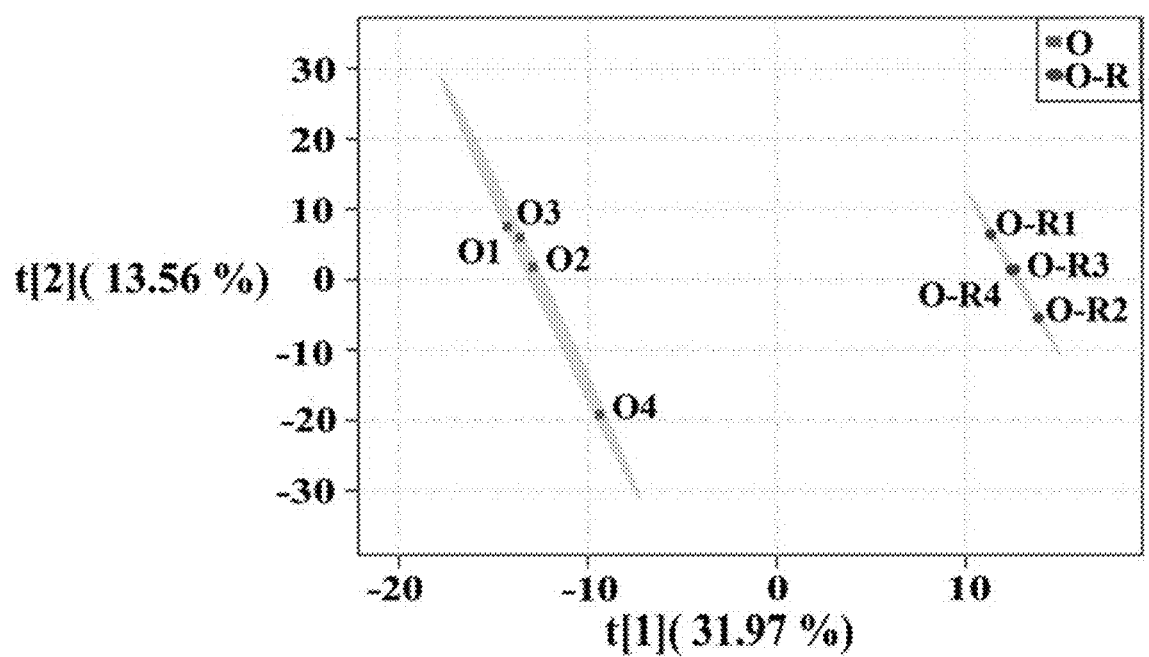
FIG. 2C is the PLS-DA diagram of OCI-LY10-S and OCI-LY10-R.
Figure 3A:
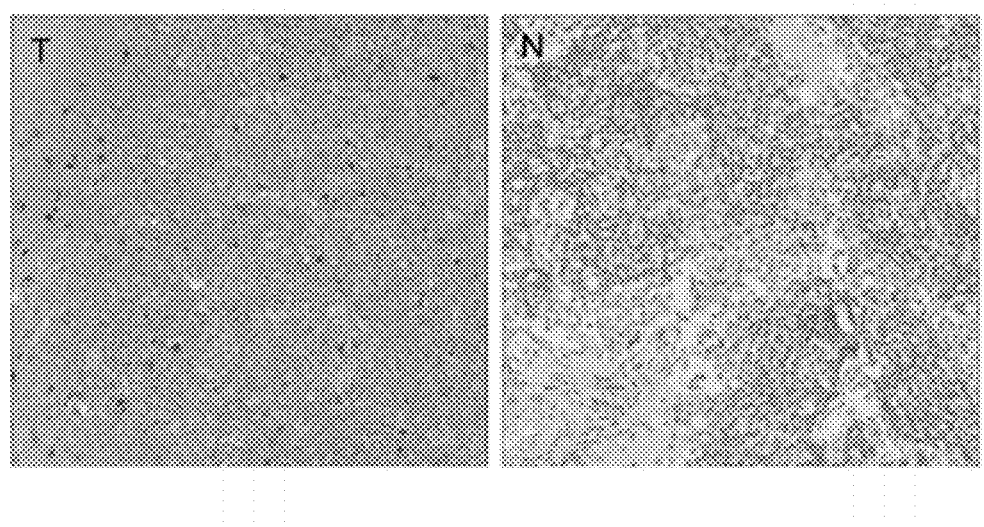
FIG. 3A shows the expressions of SMPD1 in ABC-DLBCL tissues and normal tissues (IHC), where T is the positive expression in ABC-DLBc1 tissues (×200) and N is the negative expression in normal tissues (×200).
Figure 3C:
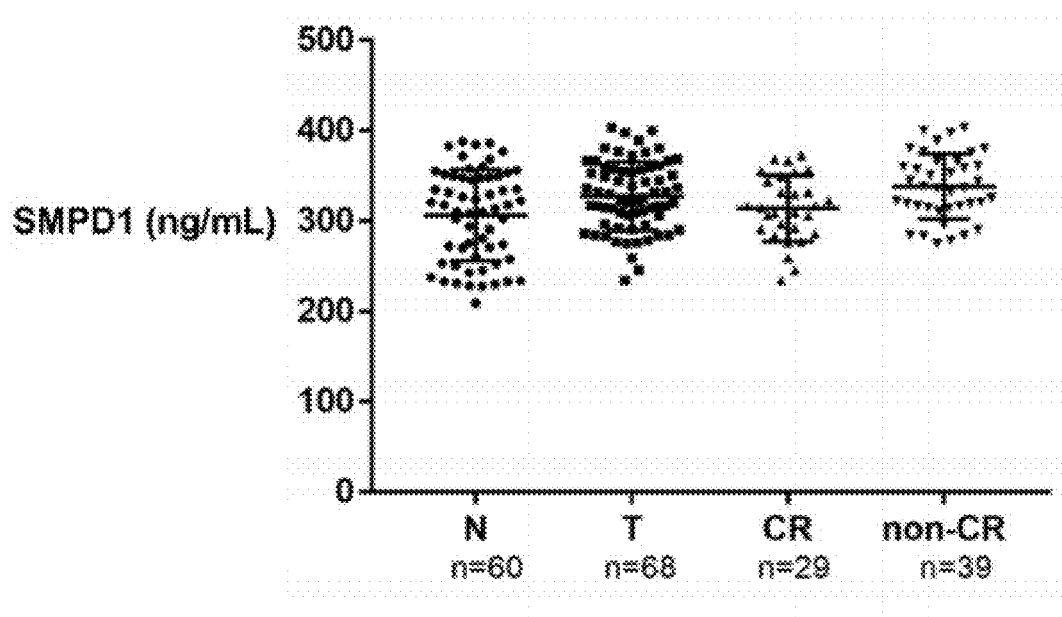
FIG. 3C shows the comparative results of SMPD1 concentration levels in pre-treatment, post-treatment CR, post-treatment non-CR, and normal human serum in ABC-DLBCL patients treated with zebutinib combination chemotherapy after R-CHOP resistance.
Figure 3D:
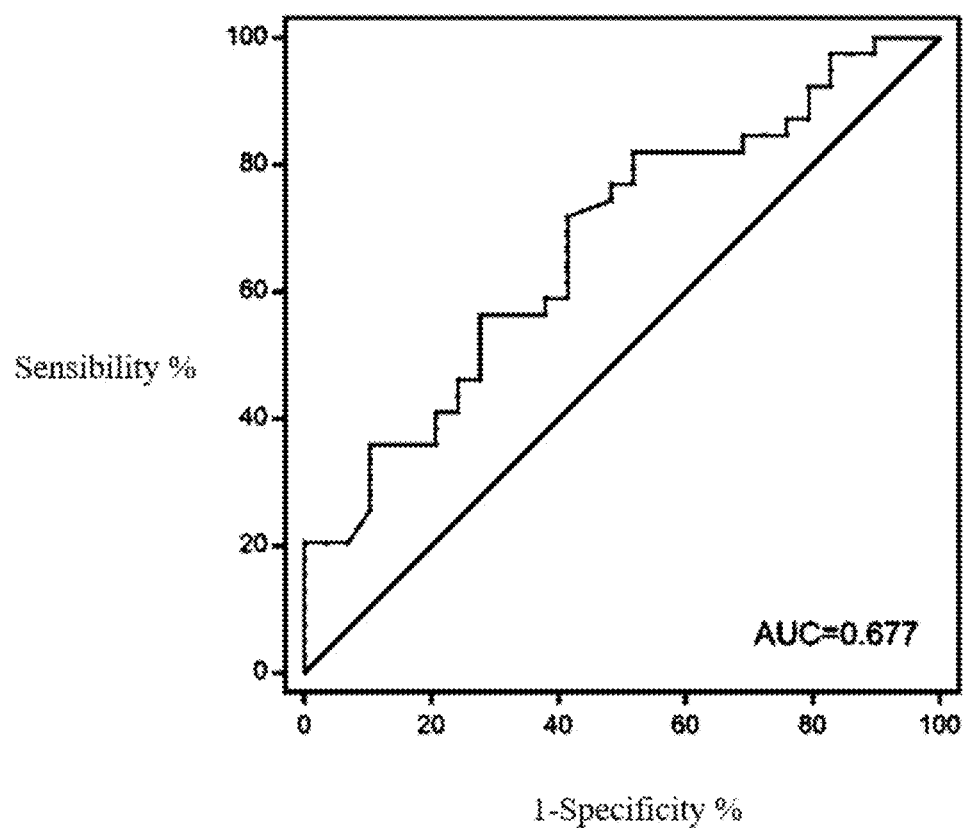
FIG. 3D is the subject operating characteristic curve: serum levels of SMPD1 to evaluate the specificity and sensitivity of CR.

Ultra-performance liquid chromatography combined with mass spectrometry is used to detect the parental ABC-DLBCL cell line and BTK inhibitor resistant ABC-DLBCL cell line. According to OPLS-DA model, the metabolites with multi-dimensional statistical analysis VIP>1 and univariate statistical analysis P<0.05 are selected as the metabolites with significant differences. A total of 42 substances are screened out by crossing the metabolic differences of the three groups of parents/drug resistance (FIG. 2A-FIG. 2C). Further, the double cluster analysis of hierarchical clustering and KEGG genome pathway and function analysis of the three groups of differential metabolites show that there are significant differences in sphingomyelin metabolism of BTK inhibitor-resistant ABC-DLBCL cell lines.

2.2 Significant Elevation of SMPD1 Levels in Tissue and Serum of Patients after BTK Inhibitor Treatment and Correlation with Efficacy Immunohistochemical method is used to analyze the expression of SMPD1 in 68 cases of ABC-DLBCL after R-CHOP resistance and zebutinib combined with chemotherapy. The results show that SMPD1 is located in the cytoplasm, and the expression intensity of SMPD1 is significantly different from that of clinical complete remission (CR) (P=0.038), showing a significant negative correlation. There is also significant difference between serum SMPD1 level and CR level in the above patients (P=0.008), suggesting that the increase of SMPD1 in tissues and serum has potential value in evaluating curative effect (see FIG. 3A-FIG. 3E).

Figure 4A:
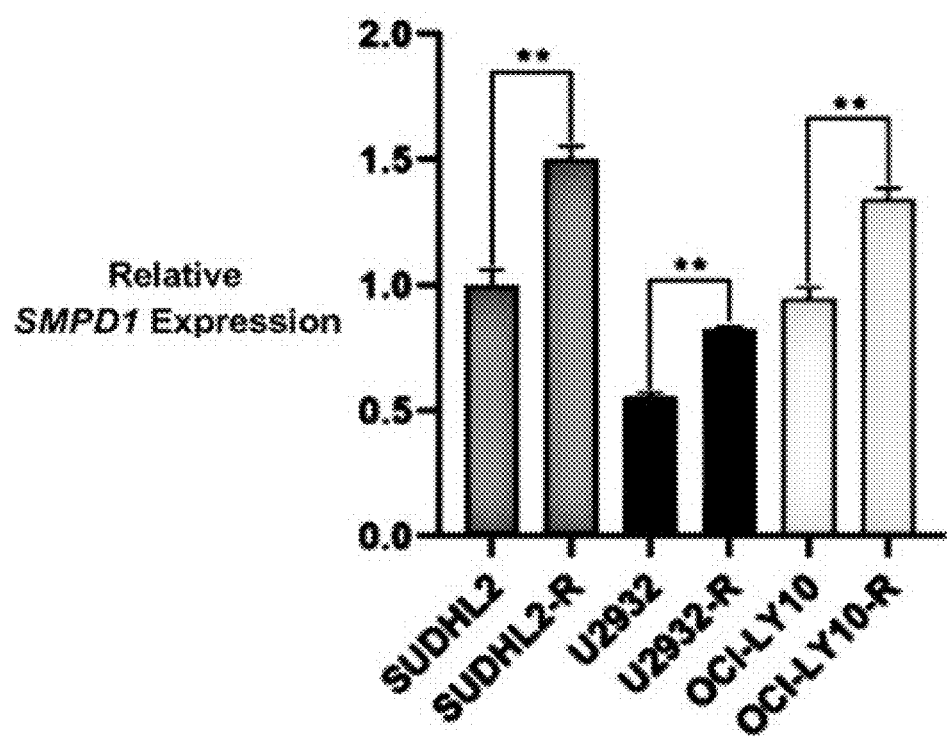
FIG. 4A shows the detection results of SMPD1 transcription level of drug-resistant/sensitive cell lines.
Figure 4B:
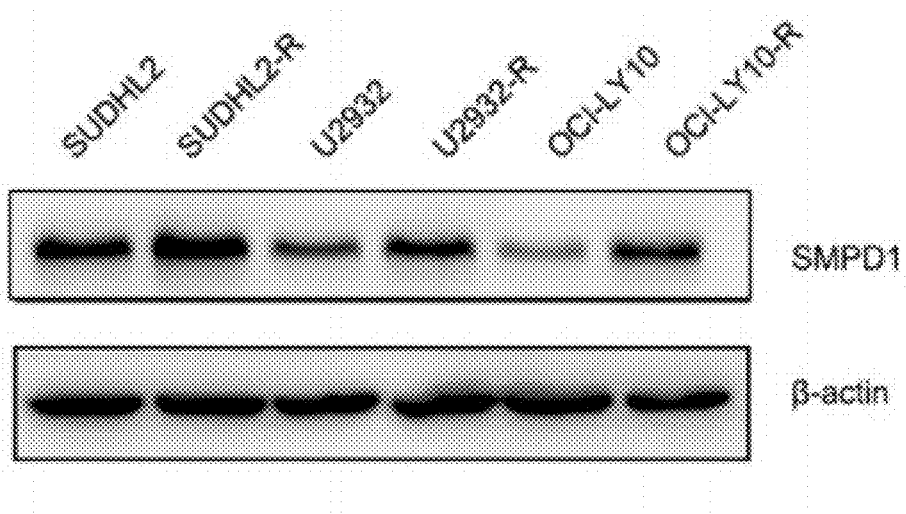
FIG. 4B illustrates the detection results of SMPD1 translation level of drug-resistant/sensitive cell lines.
Figure 4C:
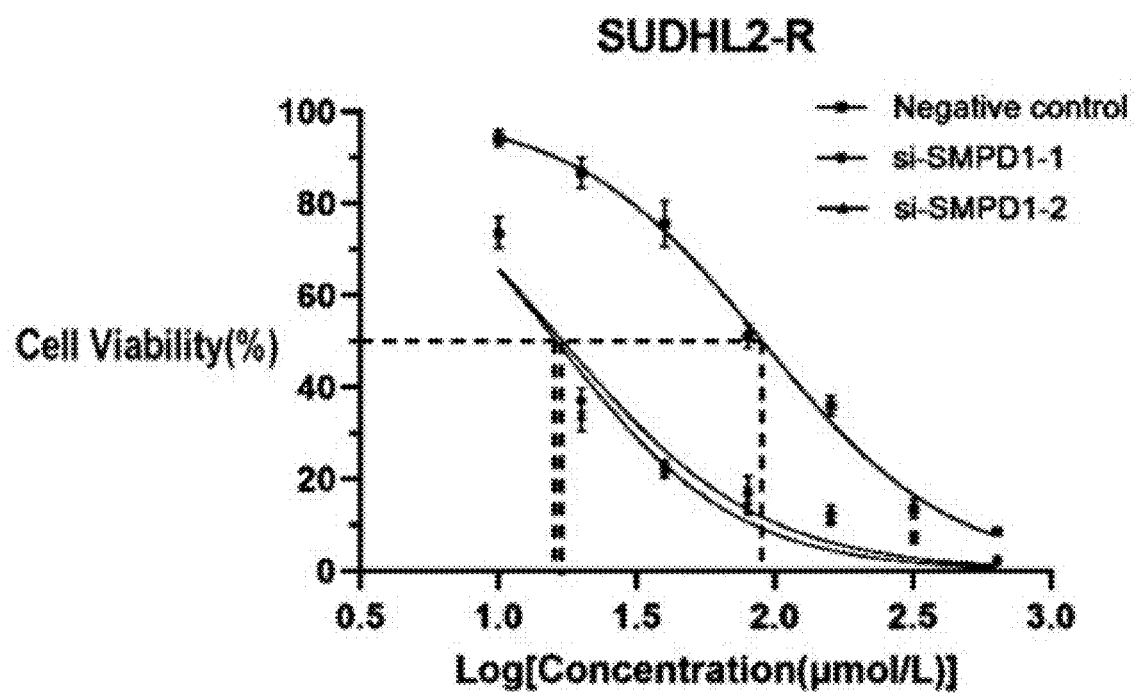
FIG. 4C shows the $IC_{50}$ curve of zebutinib in the BTK inhibitor-resistant ABC-DLBCL cell line SUDHL2-R after knockdown of SMPD1.
Figure 4D:
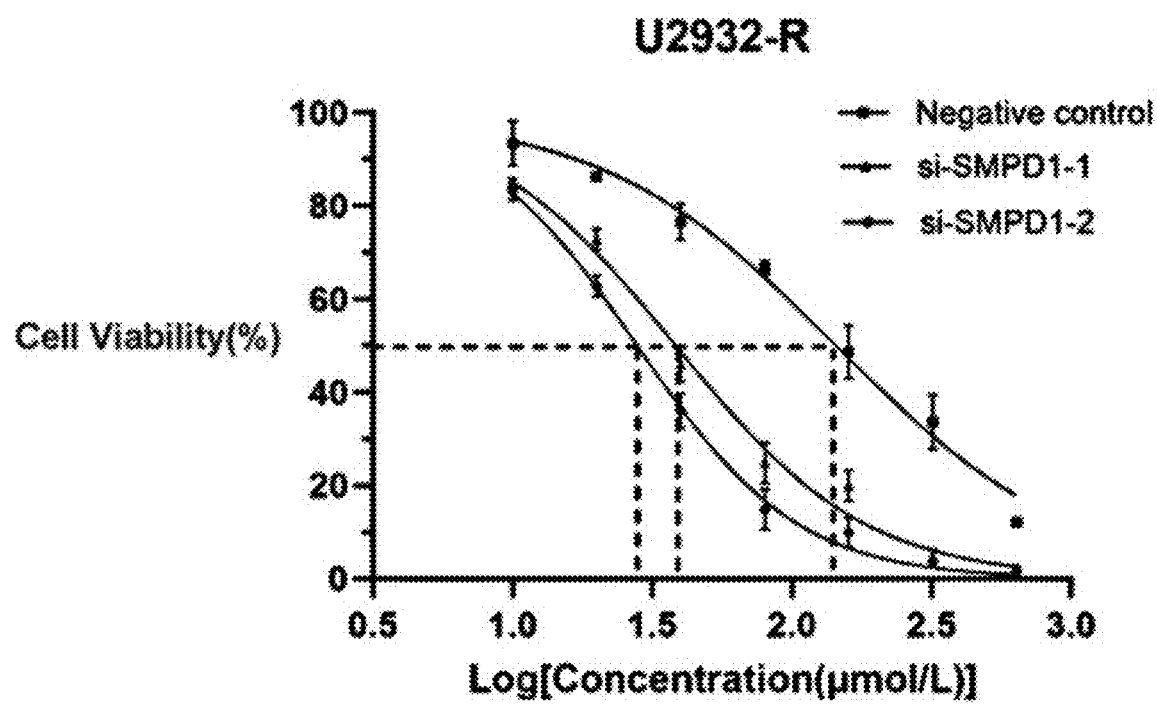
FIG. 4D shows the $IC_{50}$ curve of zebutinib in the BTK inhibitor-resistant ABC-DLBCL cell line U2932-R after knockdown of SMPD1.
Figure 4E:
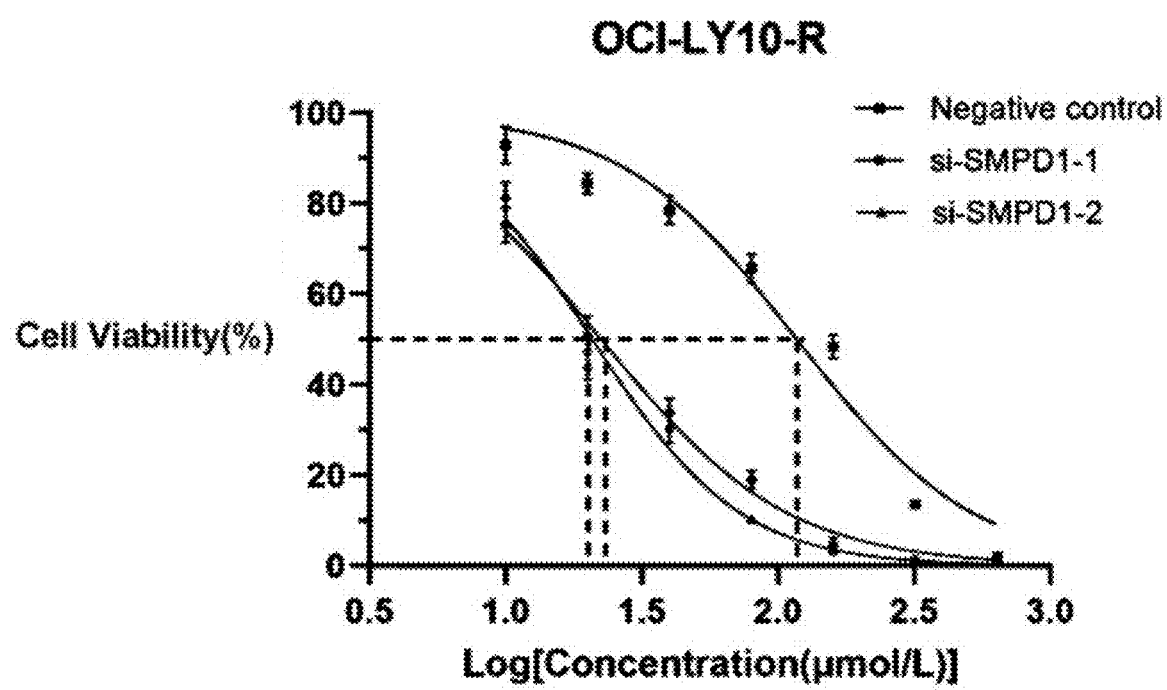
FIG. 4E shows the $IC_{50}$ curve of zebutinib in the BTK inhibitor-resistant ABC-DLBCL cell line OCI-LY10-R after knockdown of SMPD1.
Figure 4F:
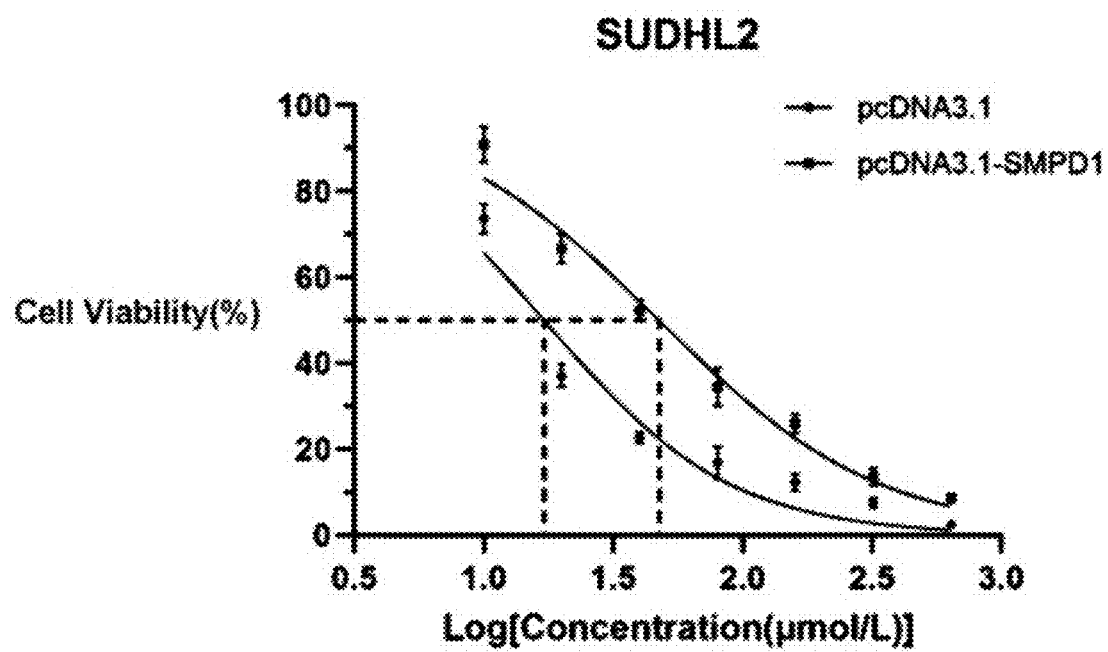
FIG. 4F shows the $IC_{50}$ curve of zebutinib after SMPD1 overexpression in BTK inhibitor-sensitive ABC-DLBCL cell line SUDHL2.
Figure 4G:
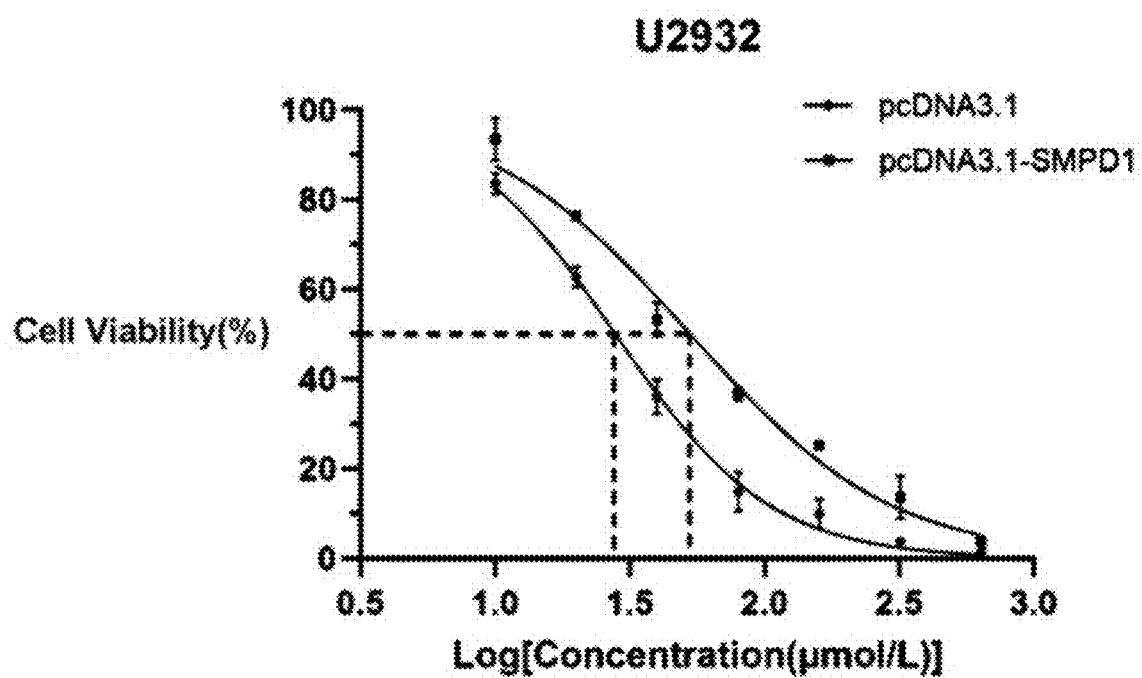
FIG. 4G shows the $IC_{50}$ curve of zebutinib after SMPD1 overexpression in BTK inhibitor-sensitive ABC-DLBCL cell line U2932.
Figure 4H:
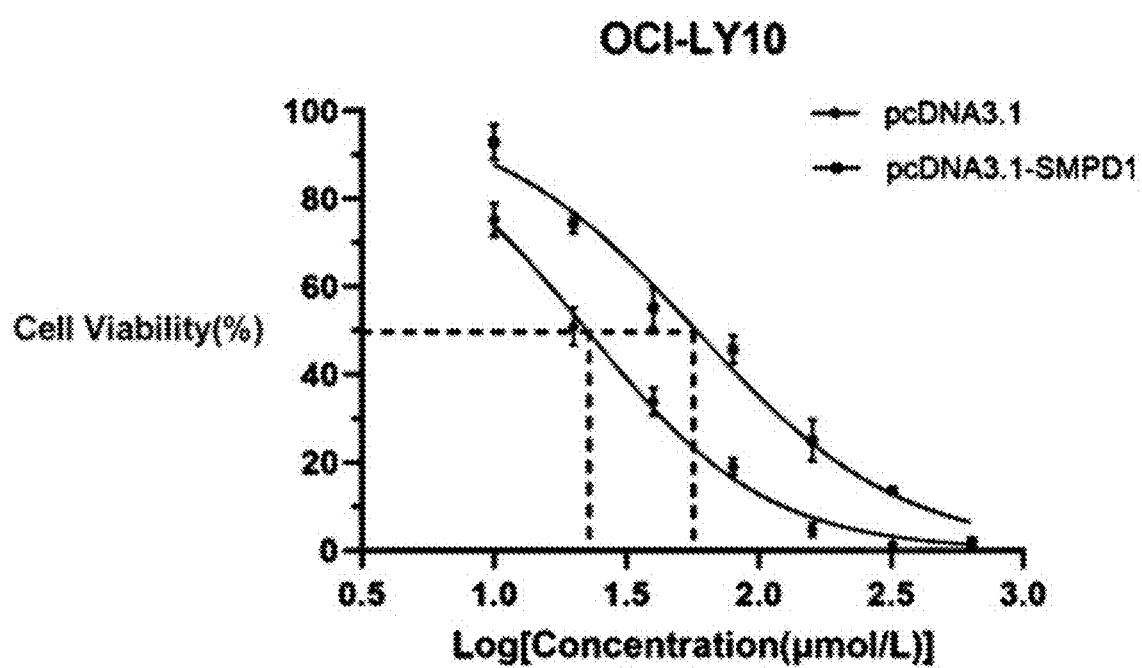
FIG. 4H shows the $IC_{50}$ curve of zebutinib after SMPD1 overexpression in BTK inhibitor-sensitive ABC-DLBCL cell line OCI-LY10.
Figure 4I:
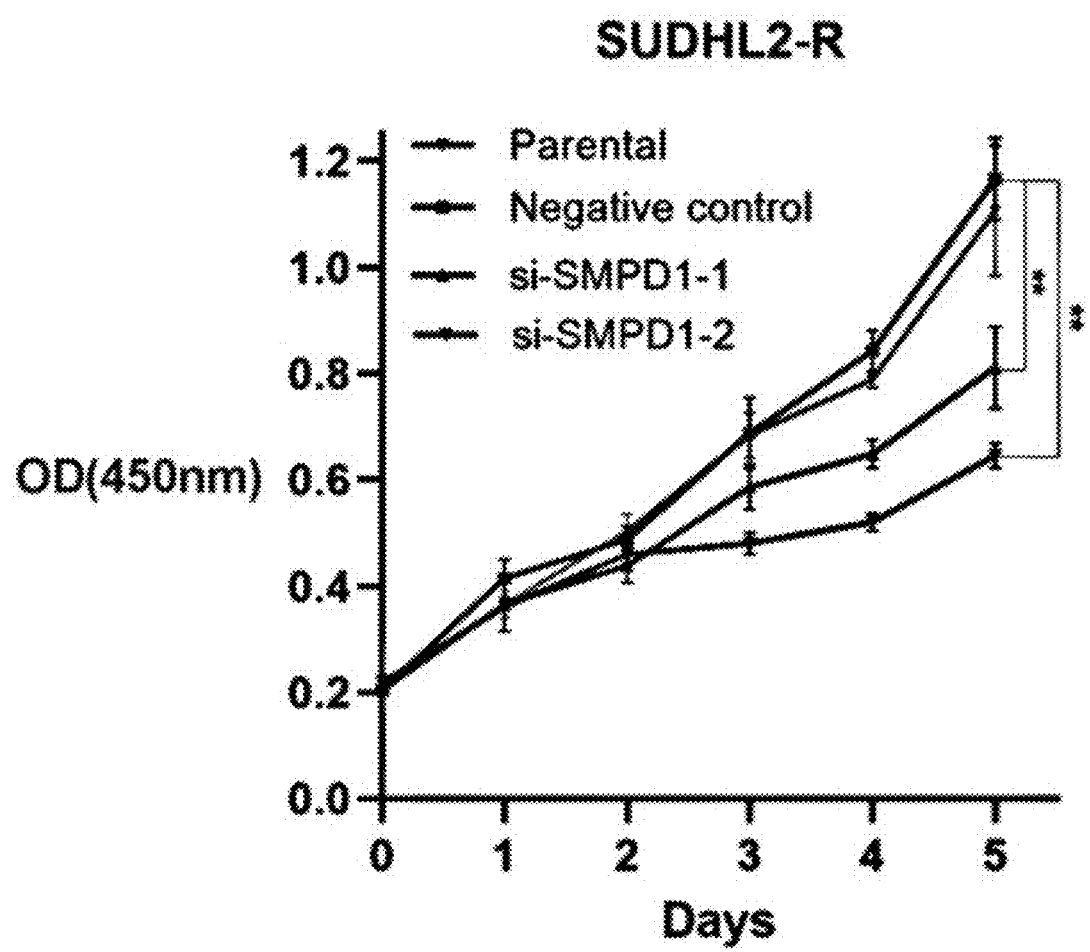
FIG. 4I shows the cell growth curve of BTK inhibitor-resistant ABC-DLBCL cell line SUDHL2-R after SMPD1 knockdown.
Figure 4J:
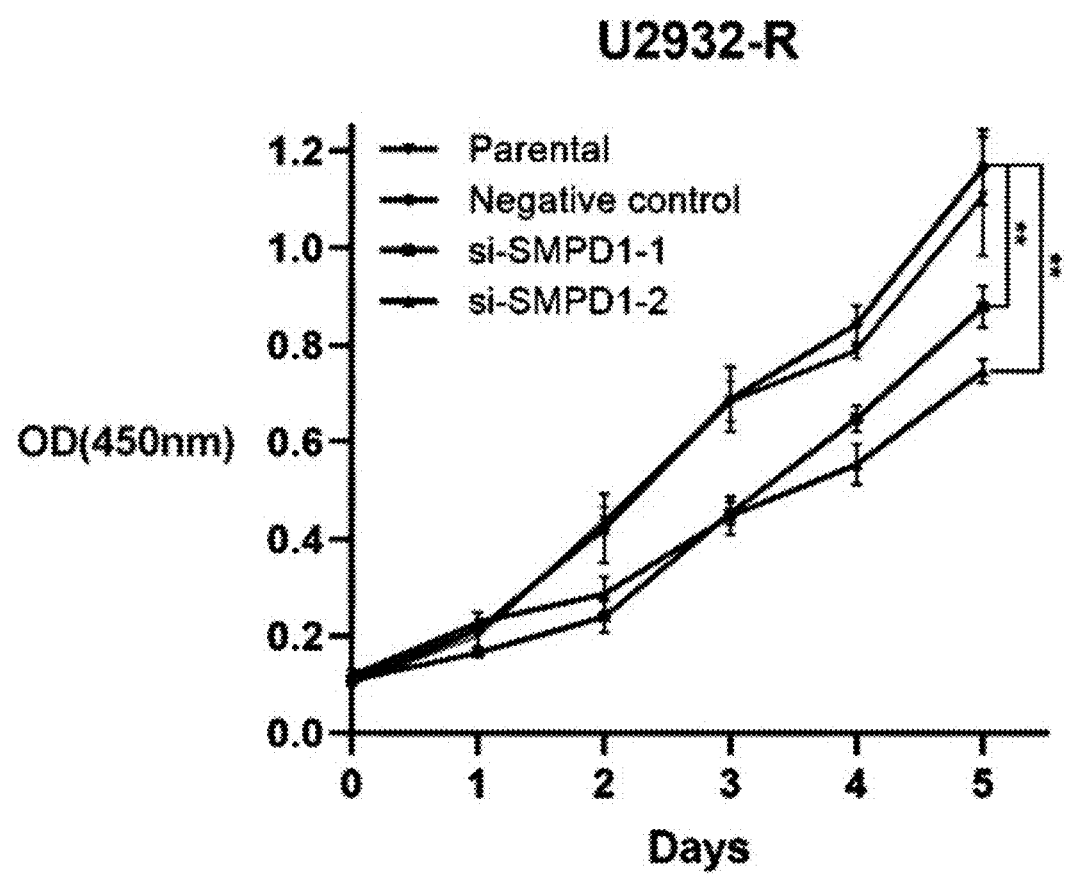
FIG. 4J shows the cell growth curve of BTK inhibitor-resistant ABC-DLBCL cell line U2932-R after SMPD1 knockdown.
Figure 4K:
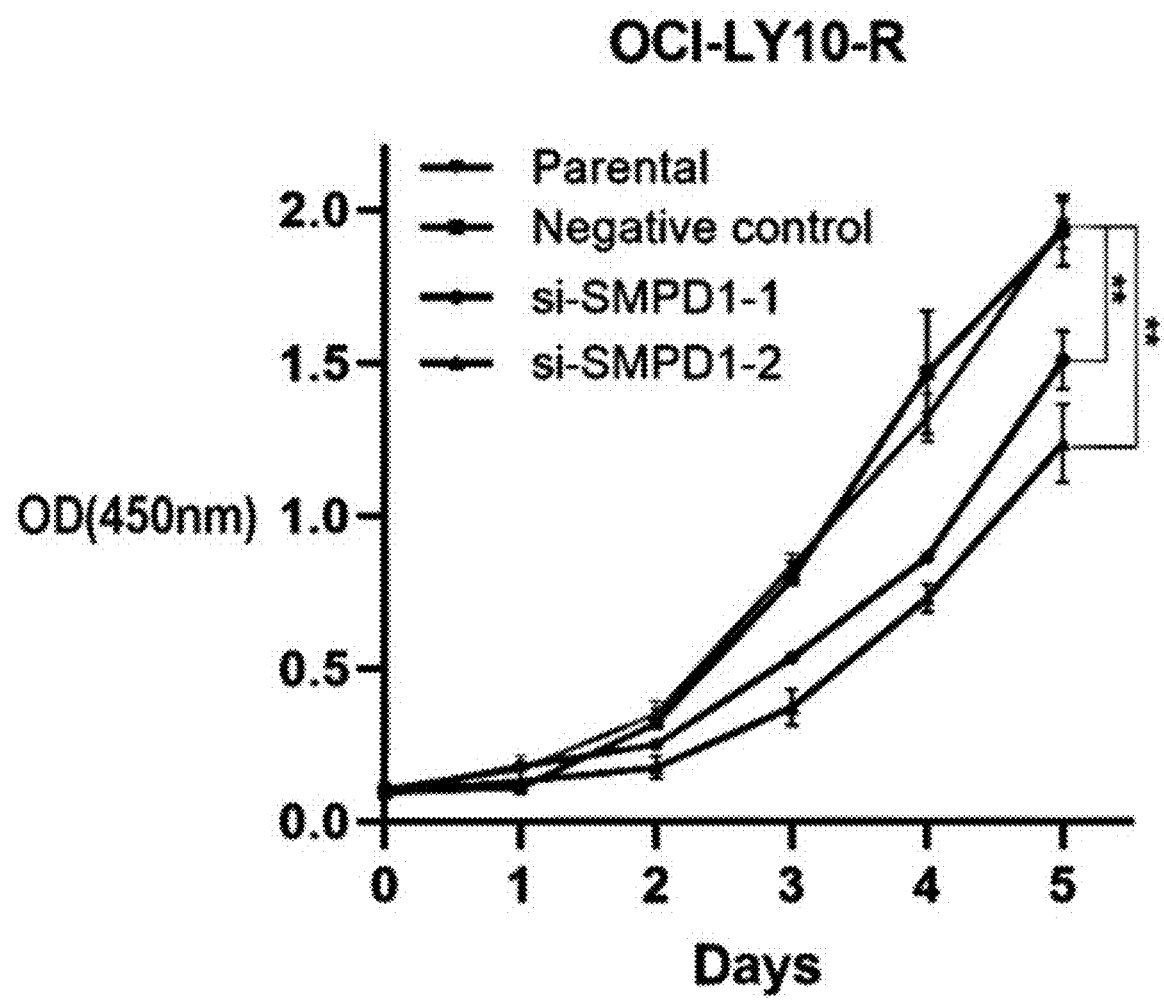
FIG. 4K shows the cell growth curve of BTK inhibitor-resistant ABC-DLBCL cell line OCI-LY10-R after SMPD1 knockdown.
Figure 4L:
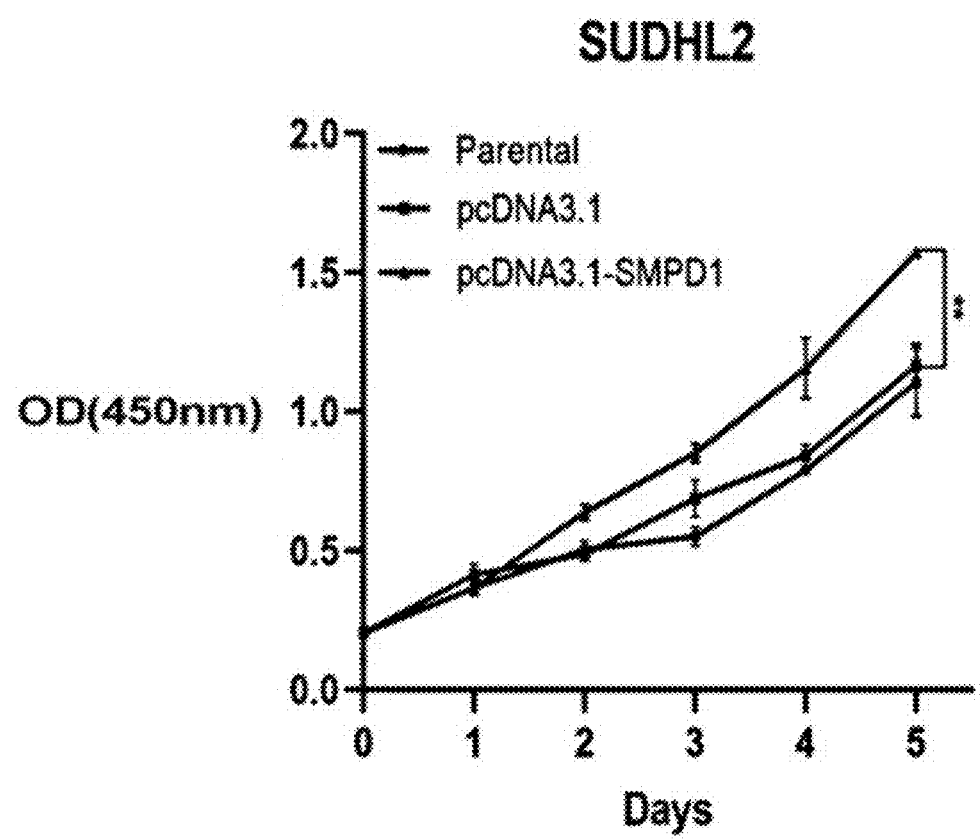
FIG. 4L shows the cell growth curve of BTK inhibitor-sensitive ABC-DLBCL cell line SUDHL2 after SMPD1 overexpression.
Figure 4M:
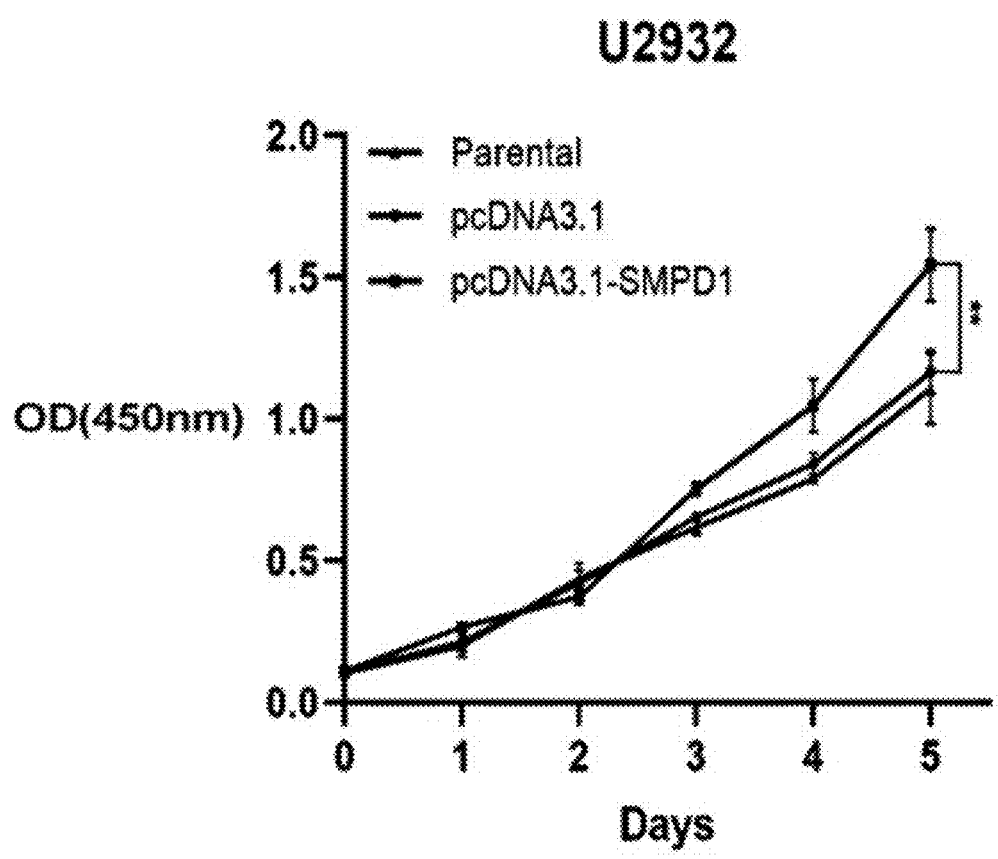
FIG. 4M shows the cell growth curve of BTK inhibitor-sensitive ABC-DLBCL cell line U2932 after SMPD1 overexpression.
Figure 4N:
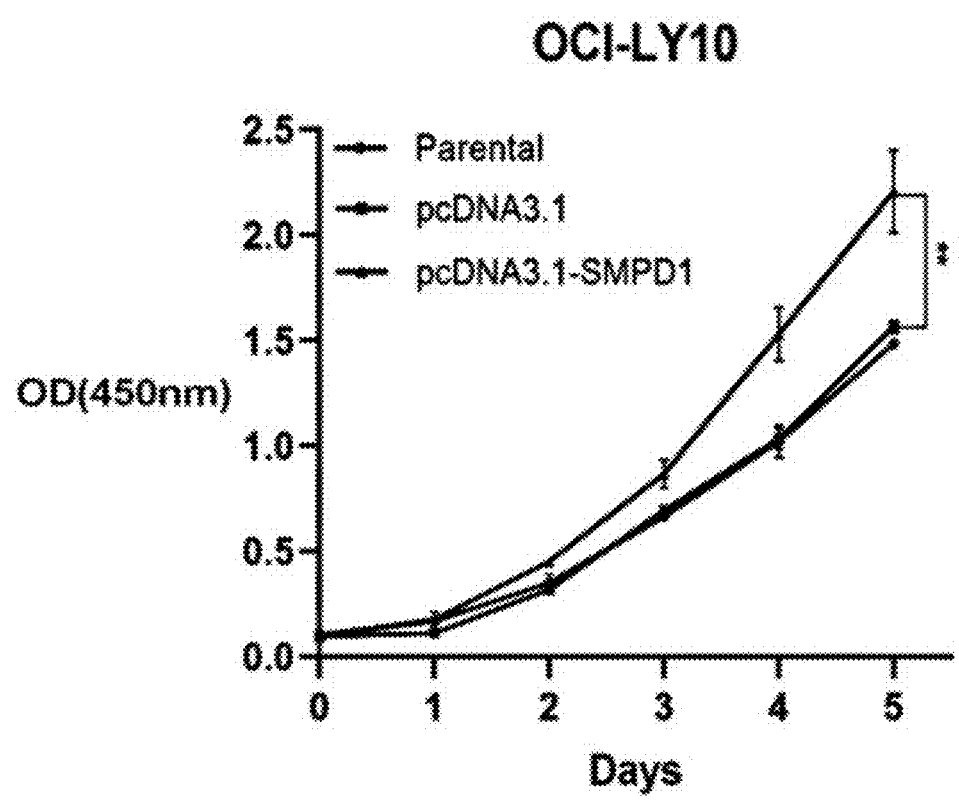
FIG. 4N shows the cell growth curve of BTK inhibitor-sensitive ABC-DLBCL cell line OCI-LY10 after SMPD1 overexpression.

2.3 High Expression of SMPD1 Promoting the Proliferation and Drug Resistance of ABC-DLBCL Tumor Cells The mRNA and protein expression of SMPD1 in ABC-DLBCL cell lines in vitro show that the expression levels of SMPD1 in drug-resistant cell lines SUDHL2-R, U2932-R and OCI-LY10-R are significantly higher than those in sensitive cell lines, suggesting that the transcription and translation levels of SMPD1 in BTK inhibitor-resistant ABC-DLBCL cell lines are significantly enhanced (see FIG. 4A-FIG. 4N). The drug-resistant cell lines SUDHL2-R, U2932-R and OCI-LY10-R with knockdown of SMPD1 show a significant decrease in $IC_{50}$ compared to the negative control; sensitive cell lines SUDHL2, U2932 and OCI-LY10 over-expressing SMPD1 shows a significant increase in $IC_{50}$ compared to no load, indicating that SMPD1 plays an important role in the enhancement of BTK inhibitor resistance in ABC-DLBCL (see FIG. 4C); drug-resistant cell lines SUDHL2-R, U2932-R, and OCI-LY10-R with knockdown of SMPD1 results in significant inhibition of cell proliferation compared to the control group; after knockdown of SMPD1 in drug-resistant cell lines SUDHL2-R, U2932-R and OCI-LY10-R, cell proliferation is significantly inhibited compared to the control group; after over-expression of SMPD1 in sensitive cell lines SUDHL2, U2932 and OCI-LY10, cell proliferation is significantly enhanced compared to the control group; demonstrating that SMPD1 promotes tumor cell ABC-DLBCL proliferation (see FIG. 4D).

Figure 5A:
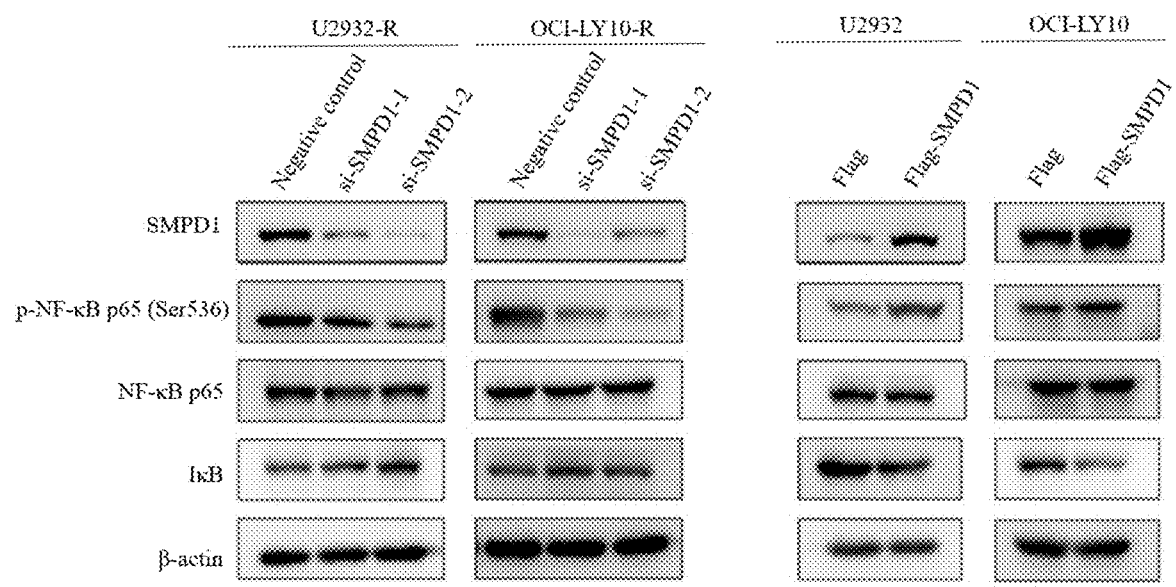
FIG. 5A shows the detection results of the expression levels of p-NF-κB p65, NF-κB p65 and IκB after the drug-resistant cell lines U2932-R and OCI-LY10-R knocked down SMPD1.
Figure 5B:
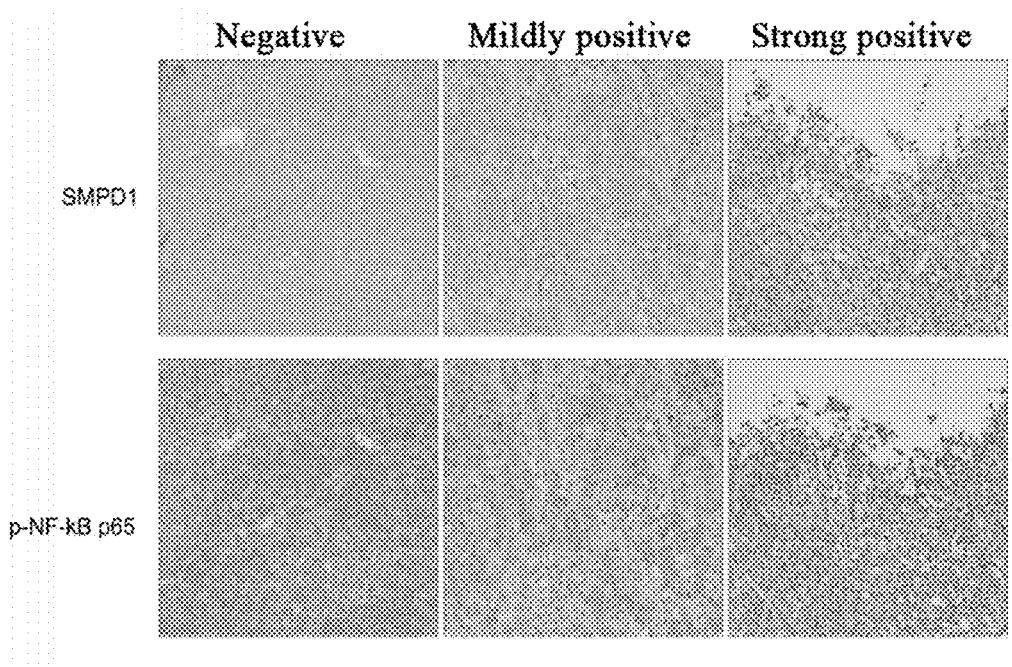
FIG. 5B illustrates the expression detection results of SMPD1 and p-NF-κB p65 in the same position of ABC-DLBCL tumor tissue, with a scale of 100 micrometer (μm).

2.4 Up-Regulation of ABC-DLBCL Resistance by SMPD1 Through Phosphorylation of NF-κB and Consequent Enhancement of NF-κB Nuclear Expression In order to investigate the molecular mechanisms by which SMPD1 affects the therapeutic response and prognosis of ABC-DLBCL, the present disclosure demonstrates that by knocking down/over-expressing SMPD1, the p-NF-κB p65 is down-regulated, NF-κBp65 is unchanged, and the IκB is up-regulated in the drug-resistant cell lines U2932-R, and OCI-LY10-R after knocking down SMPD1, and in the sensitive cell lines U2932, and OCI-LY10 over-expressing SMPD1, the p-NF-κB p65 is up-regulated, NF-κBp65 is unchanged, and IκB is down-regulated (see FIG. 5A), evidencing that rather than activating NF-κB by degrading the IκB pathway, SMPD1 may up-regulate its activity by phosphorylating NF-κB, which in turn enhances the nuclear expression of NF-κB, and modulates the resistance to ABC-DLBCL; moreover, SMPD1 and p-NF-κB p65 are co-expressed at high levels in ABC-DLBCL tumor tissues (see FIG. 5B), indicating that SMPD1 may have a regulatory function over p-NF-κBp65.

Figure 6A:
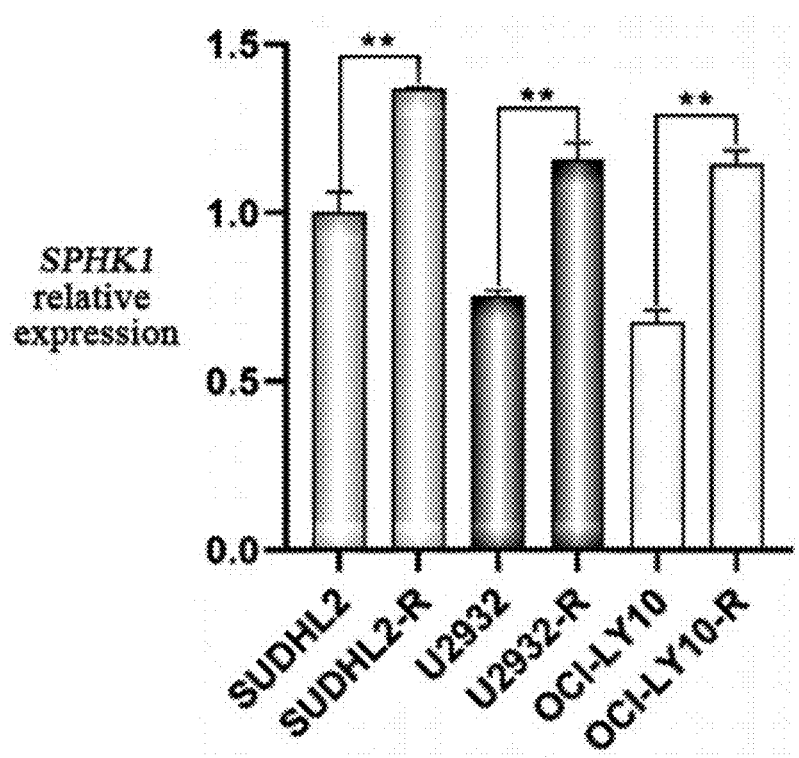
FIG. 6A shows the detection results of SPHK1 transcription levels of drug-resistant/sensitive cell lines.
Figure 6B:
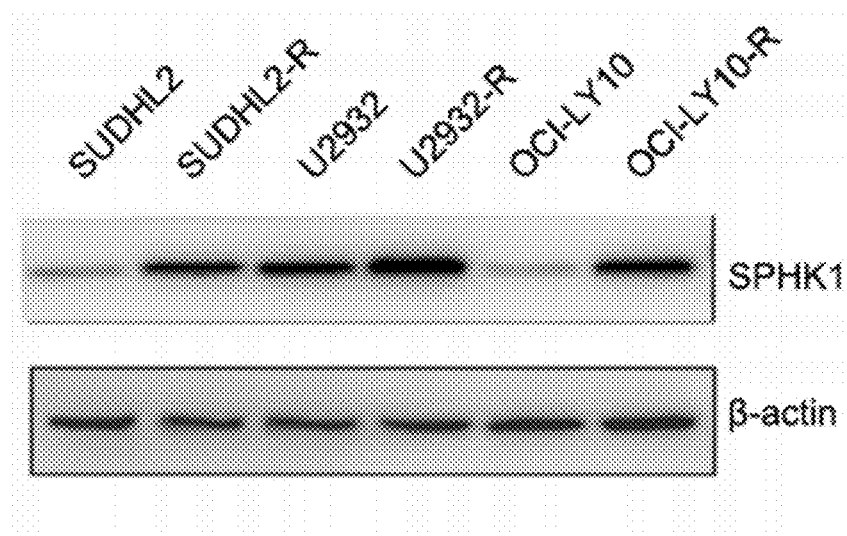
FIG. 6B shows the detection results of SPHK1 translation levels of drug-resistant/sensitive cell lines.
Figure 6C:
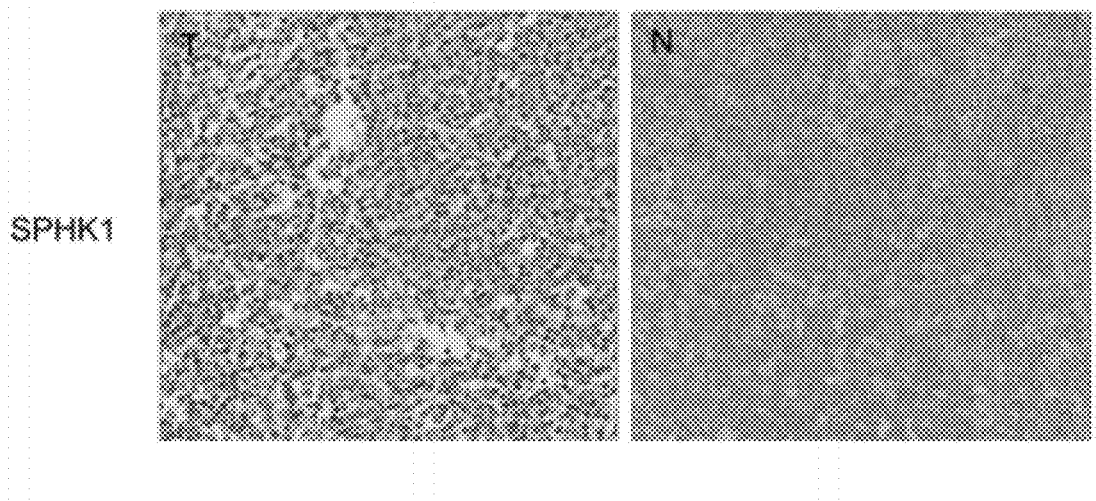
FIG. 6C illustrates the detection results of SPHK1 expression (IHC) in ABC-DLBCL tissue and normal tissue, where T shows ABC-DLBCL tissue positive expression (×200) and N shows negative expression in normal tissues (×200).
Figure 6D:
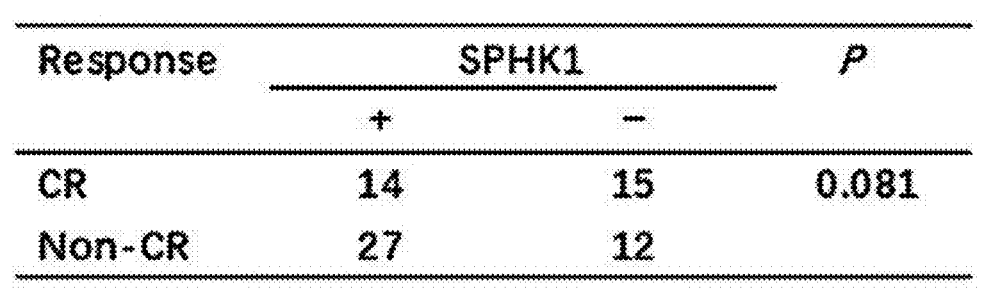
Figure 6E:
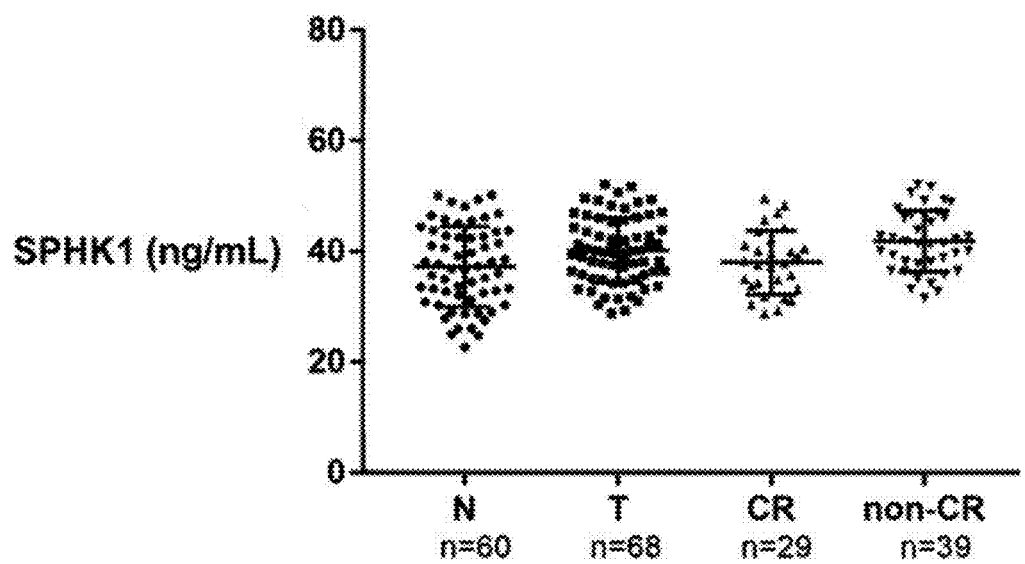
FIG. 6E shows the comparative results of pre-treatment, post-treatment CR, post-treatment non-CR, and normal human serum levels of SPHK1 concentration in ABC-DLBCL patients treated with zebutinib combination chemotherapy after R-CHOP resistance.
Figure 6F:
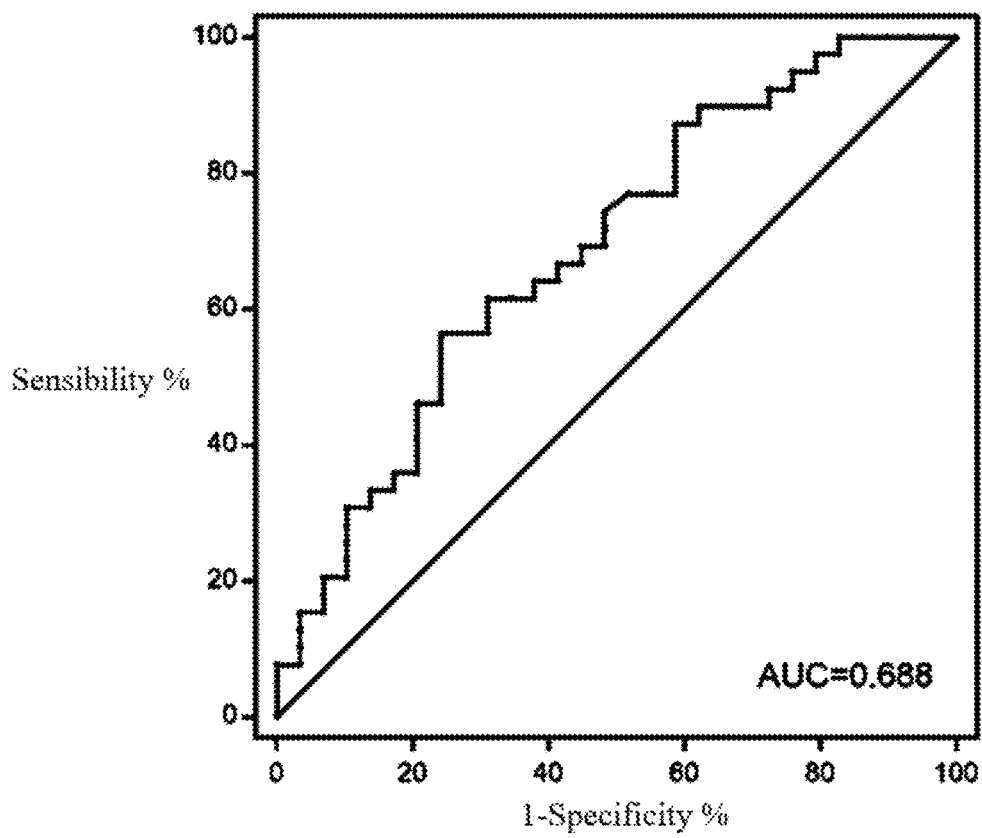
FIG. 6F is the receiver operating characteristic curve: the specificity and sensitivity of serum SPHK1 in evaluating CR.
Figure 6H:
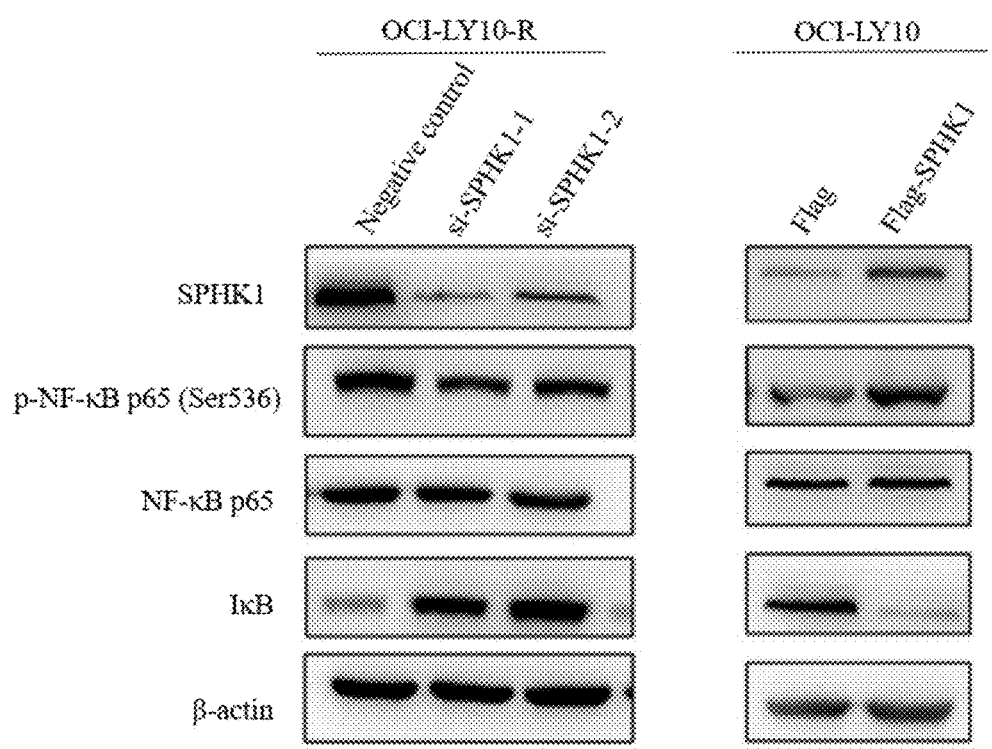
FIG. 6H shows the detection results of the expression levels of p-NF-κB p65, NF-κB P65 and IκB after the drug-resistant/sensitive cell line OCI-LY10-R knocks down/over-expresses SPHK1, with a scale of 100 μm.

2.5 Activation of NF-κB by SMPD1/NF-κB Pathway Through the Intermediate Molecule SPHK1 and Association of SPHK1 with Therapeutic Efficacy To further explore SMPD1-interacting molecules, SMPD1-interacting proteins detected by bioinformatics analysis and Western Blot are utilized to search for molecules with transcriptional regulatory functions. Then, peptides that bind to SMPD1 are captured and sequenced by GST-pull down and mass spectrometry (MS), and the measured peptide profiles are compared with the database to obtain candidate proteins that may bind to SMPD1, and the interaction relationship between SMPD1 and the downstream molecules is verified by experiments such as Co-IP. Then, the rescue experiment is carried out to verify the effects of SMPD1 interacting molecules on the phenotype of ABC-DLBCL cells and the sensitivity of BTK inhibitors, and the results show that the expression levels of SPK1 in drug-resistant cell lines SUDHL2-R, U2932-R and OCI-LY10-R are significantly higher than those in sensitive cell lines, suggesting that the transcription and translation levels of BTK inhibitor-resistant ABC-DLBCL cell line SPK1 are significantly enhanced (see FIG. 6A and FIG. 6B); and by analyzing the expression (IHC) of SPHK1 in ABC-DLBCL tissues and normal tissues, it is found that SPHK1 is positively expressed in ABC-DLBCL tissues (×200) (see FIG. 6C); however, it is negative in normal tissues; after further analysis, a trend of negative correlation between high SPHK1 protein expression (IHC) and clinical complete remission (CR) is identified (see FIG. 6D); by comparing the levels of SPHK1 concentration in serums of ABC-DLBCL patients before R-CHOP-resistant chemotherapy combined with zebutinib, CR after treatment, non-CR after treatment, and normal subjects, the results indicate that the concentration of SPHK1 in serums is significantly negatively correlated with the CR (see FIG. 6E, FIG. 6F, and FIG. 6G); after knockdown of SPHK1 in the drug-resistant cell line OCI-LY10-R, the p-NF-κB p65 is down-regulated, NF-κB p65 remains unchanged, and IκB is up-regulated; the p-NF-κBp65 is up-regulated, NF-κB p65 remains unchanged, and IκB is down-regulated after the sensitive cell line OCI-LY10 over-expressing SPHK1, suggesting that SPHK1 may not activate NF-κB by degrading IκB, but up-regulate its activity by phosphorylating NF-κB, thus enhancing the nuclear expression of NF-κB and regulating the drug resistance of ABC-DLBCL (see FIG. 6H).

In summary, the present disclosure identifies significant differences in the occurrence of sphingolipid metabolism where SMPD1 is located in BTK inhibitor-resistant ABC- DLBCL cell lines through the establishment of BTK inhibitor-resistant cell lines in the preliminary stage as well as the screening and analysis of metabolic differentials in parental/resistant cells. Subsequently, the effect of SMPD1 on the development of BTK inhibitor resistance in ABC-DLBCL is determined by IHC and ELISA, and the molecular mechanism of SMPD1-mediated development of BTK inhibitor resistance in ABC-DLBCL is further analyzed by knockdown/over-expression of SMPD1 and other experiments, which confirms that the high expression of SMPD1 is capable of promoting the tumor cell proliferation and drug resistance of ABC-DLBCL and up-regulating its activity through the phosphorylation of NF-κB by the intermediate molecule SPHK1, which in turn enhances the nuclear expression of NF-κB, thus regulating the development of drug resistance in ABC-DLBCL. The results of the present disclosure further improve the understanding of ABC-DLBCL BTK inhibitor resistance mechanism and improve the status quo of BTK inhibitor resistance, confirming that SMPD1 and SPHK1 are very promising therapeutic targets for BTK inhibitor resistance, and providing new ideas for the development of new targeted drugs.

The present disclosure investigates the mechanism of ABC-DLBCL BTK inhibitor resistance, and the results show that the SMPD1/NF-κB signaling pathway exists and is involved in the regulation of BTK inhibitor resistance, and the study further reveals the role of SMPD1 in anti-tumor immunity, which is expected to change the current status quo of BTK inhibitor resistance in patients with R/R ABC-DLBCL, and thereby improve the prognosis of patients. The present disclosure discovers the relationship between SMPD1 and BTK inhibitor drug resistance, provides a treatment method of combining SMPD1 or SPHK1 inhibitor with BTK inhibitor to treat ABC-DLBCL, and promotes the research on the drug resistance mechanism and combined medication of ABC-DLBCL BTK inhibitor.

The abnormal changes of key molecules in SMPD1/NF-κB signaling pathway have the potential to be a dynamic monitoring marker of BTK inhibitor resistance, and are expected to be a factor in the mid-term evaluation of therapeutic schemes, and to predict the final outcome of treatment. This marker is utilized for prediction, both to facilitate the rational selection of second-line therapy after treatment failure of R-CHOP-like regimens, taking into account the efficacy of treatment while focusing on the cost-effectiveness of treatment, and is expected to be a factor in the midterm evaluation of therapeutic regimens and prognostication of the final outcome of treatment.

The above-mentioned embodiments only describe the preferred mode of the disclosure, and do not limit the scope of the disclosure. Under the premise of not departing from the design spirit of the disclosure, various modifications and improvements made by ordinary technicians in the field to the technical scheme of the disclosure shall fall within the protection scope determined by the claims of the disclosure.

What is claimed is:

1. A composition for treating diffuse large B cell lymphoma comprising a reagent for reducing an expression of sphingomyelin phosphodiesterase 1 (SMPD11) and/or sphingosine kinase 1 (SPHK11) and a Bruton's tyrosine kinase (BTK inhibitor; wherein the reagent is short hairpin ribonucleic acid (shRNA) with a nucleotide sequence as shown in SEQ ID NO.6; and the BTK inhibitor is zebutinib.

* * * * *

```
SEQUENCE LISTING

Sequence total quantity: 22
SEQ ID NO: 1              moltype = RNA  length = 23
FEATURE                   Location/Qualifiers
source                    1..23
                          mol_type = other RNA
                          organism = synthetic construct
SEQUENCE: 1
gccacactca tgtggatgaa ttt                                         23

SEQ ID NO: 2              moltype = RNA  length = 23
FEATURE                   Location/Qualifiers
source                    1..23
                          mol_type = other RNA
                          organism = synthetic construct
SEQUENCE: 2
attcatccac atgagtgtgg ctt                                         23

SEQ ID NO: 3              moltype = RNA  length = 21
FEATURE                   Location/Qualifiers
source                    1..21
                          mol_type = other RNA
                          organism = synthetic construct
SEQUENCE: 3
cagggctcga gaaacctatt t                                           21

SEQ ID NO: 4              moltype = RNA  length = 21
FEATURE                   Location/Qualifiers
source                    1..21
                          mol_type = other RNA
                          organism = synthetic construct
SEQUENCE: 4
ataggtttct cgagccctgt t                                           21

SEQ ID NO: 5              moltype = RNA  length = 23
FEATURE                   Location/Qualifiers
source                    1..23
                          mol_type = other RNA
                          organism = synthetic construct
SEQUENCE: 5
gcagcttcct tgaaccatta ttt                                         23

SEQ ID NO: 6              moltype = RNA  length = 23
```

```
FEATURE              Location/Qualifiers
source               1..23
                     mol_type = other RNA
                     organism = synthetic construct
SEQUENCE: 6
ataatggttc aaggaagctg ctt                                              23

SEQ ID NO: 7         moltype = RNA   length = 19
FEATURE              Location/Qualifiers
source               1..19
                     mol_type = other RNA
                     organism = synthetic construct
SEQUENCE: 7
ttctccgaac gtgtcacgt                                                   19

SEQ ID NO: 8         moltype = RNA   length = 21
FEATURE              Location/Qualifiers
source               1..21
                     mol_type = other RNA
                     organism = synthetic construct
SEQUENCE: 8
cagggctcga gaaacctatt t                                                21

SEQ ID NO: 9         moltype = RNA   length = 23
FEATURE              Location/Qualifiers
source               1..23
                     mol_type = other RNA
                     organism = synthetic construct
SEQUENCE: 9
gccacactca tgtggatgaa ttt                                              23

SEQ ID NO: 10        moltype = RNA   length = 21
FEATURE              Location/Qualifiers
source               1..21
                     mol_type = other RNA
                     organism = synthetic construct
SEQUENCE: 10
gcaggcatat ggagtatgat t                                                21

SEQ ID NO: 11        moltype = RNA   length = 21
FEATURE              Location/Qualifiers
source               1..21
                     mol_type = other RNA
                     organism = synthetic construct
SEQUENCE: 11
tcatactcca tatgcctgct t                                                21

SEQ ID NO: 12        moltype = RNA   length = 21
FEATURE              Location/Qualifiers
source               1..21
                     mol_type = other RNA
                     organism = synthetic construct
SEQUENCE: 12
ggatcatcat gctatgcagt t                                                21

SEQ ID NO: 13        moltype = DNA   length = 20
FEATURE              Location/Qualifiers
source               1..20
                     mol_type = other DNA
                     organism = synthetic construct
SEQUENCE: 13
aactacttct ggatggtcag                                                  20

SEQ ID NO: 14        moltype = DNA   length = 20
FEATURE              Location/Qualifiers
source               1..20
                     mol_type = other DNA
                     organism = synthetic construct
SEQUENCE: 14
tcctgcaagt agacactaag                                                  20

SEQ ID NO: 15        moltype = DNA   length = 20
FEATURE              Location/Qualifiers
source               1..20
                     mol_type = other DNA
                     organism = synthetic construct
SEQUENCE: 15
gctgcgaagt tgagcgaaaa                                                  20
```

```
SEQ ID NO: 16          moltype = DNA  length = 16
FEATURE                Location/Qualifiers
source                 1..16
                       mol_type = other DNA
                       organism = synthetic construct
SEQUENCE: 16
ggctggaccc agtcgg                                                    16

SEQ ID NO: 17          moltype = DNA  length = 20
FEATURE                Location/Qualifiers
source                 1..20
                       mol_type = other DNA
                       organism = synthetic construct
SEQUENCE: 17
aaagcccaaa tgctgctgtg                                                20

SEQ ID NO: 18          moltype = DNA  length = 20
FEATURE                Location/Qualifiers
source                 1..20
                       mol_type = other DNA
                       organism = synthetic construct
SEQUENCE: 18
acagctcctg tcttgtctgc                                                20

SEQ ID NO: 19          moltype = DNA  length = 20
FEATURE                Location/Qualifiers
source                 1..20
                       mol_type = other DNA
                       organism = synthetic construct
SEQUENCE: 19
ctgcgcaccc tcagaattgg                                                20

SEQ ID NO: 20          moltype = DNA  length = 20
FEATURE                Location/Qualifiers
source                 1..20
                       mol_type = other DNA
                       organism = synthetic construct
SEQUENCE: 20
tgtctcctcg atcctcagca                                                20

SEQ ID NO: 21          moltype = DNA  length = 20
FEATURE                Location/Qualifiers
source                 1..20
                       mol_type = other DNA
                       organism = synthetic construct
SEQUENCE: 21
gagcacagag cctcgccttt                                                20

SEQ ID NO: 22          moltype = DNA  length = 21
FEATURE                Location/Qualifiers
source                 1..21
                       mol_type = other DNA
                       organism = synthetic construct
SEQUENCE: 22
tcatcatcca tggtgagctg g                                              21
```